United States Patent [19]

Minton et al.

[11] Patent Number: 5,695,961

[45] Date of Patent: Dec. 9, 1997

[54] BI-FUNCTIONAL EXPRESSION SYSTEM

[75] Inventors: Nigel P. Minton, Salisbury; James D. B. Faulkner, Oxford, both of United Kingdom

[73] Assignee: Microbiological Research Authority, Wiltshire, Great Britain

[21] Appl. No.: 507,455

[22] PCT Filed: Feb. 25, 1994

[86] PCT No.: PCT/GB94/00373

§ 371 Date: Sep. 8, 1995

§ 102(e) Date: Sep. 8, 1995

[87] PCT Pub. No.: WO94/19472

PCT Pub. Date: Sep. 1, 1994

[30] Foreign Application Priority Data

Feb. 26, 1993 [GB] United Kingdom .................. 9303988

[51] Int. Cl.$^6$ .................. C12P 21/06; C12N 15/63; C12N 1/20; C07H 21/04

[52] U.S. Cl. .................. 435/69.1; 435/172.1; 435/252.1; 435/254.2; 435/320.1; 536/23.1; 536/24.1; 935/22; 935/23

[58] Field of Search .................. 435/69.1, 172.1, 435/252.1, 254.2, 320.1; 536/23.1, 24.1; 935/22, 23

[56] References Cited

U.S. PATENT DOCUMENTS 4,898,823  2/1990  Kingsman et al. .................. 435/172.3

OTHER PUBLICATIONS

Hartley et al., 1980, Nature 286:860–864.
Hitzeman et al., 1982, Nucleic Acids Research; 10:7791–7808.
Chambers et al., 1988, Gene 68:139–149.
Jayaram et al., 1983, Cell 34:95–104.
Anson et al., 1987, Gene 58:189–199.
Orum et al., 1992, Appl. Microbiol. Biotechnol 36:745–748.
Heusterpreute et al., 1985, Gene 34:363–366.
Hermann et al., 1992, Gene 119: 137–141.
Bonneaud et al., 1991, Yeast 7:609–615.
Hayman et al., 1993, Plasmid, 30:251–257.

Primary Examiner—Douglas W. Robinson
Assistant Examiner—Thanda Wai
Attorney, Agent, or Firm—Nixon & Vanderhye

[57] ABSTRACT

A novel expression system is provided comprising a DNA sequence containing transcriptional and translational signals that promote the over production of recombinant proteins both in bacterial hosts (e.g., *Escherichia coli*) and yeasts (e.g., *Saccharomyces cerevisiae*). The design of the expression system lends itself to a unique strategy which allows heterologous genes to be directly cloned at a position relative to the transcription/translation signals which is optimal for expression. Particularly provided are expression cassettes comprising a sequence of the invention combined with a purpose built series of plasmids wherein the utility and efficiency of the resultant expression vectors can be demonstrated to over produce protein, particularly phenylalanine ammonia lyase (herein abbreviated to PAL), in *E. coli* and *S. cerevisiae* to levels hitherto unattainable.

17 Claims, 9 Drawing Sheets

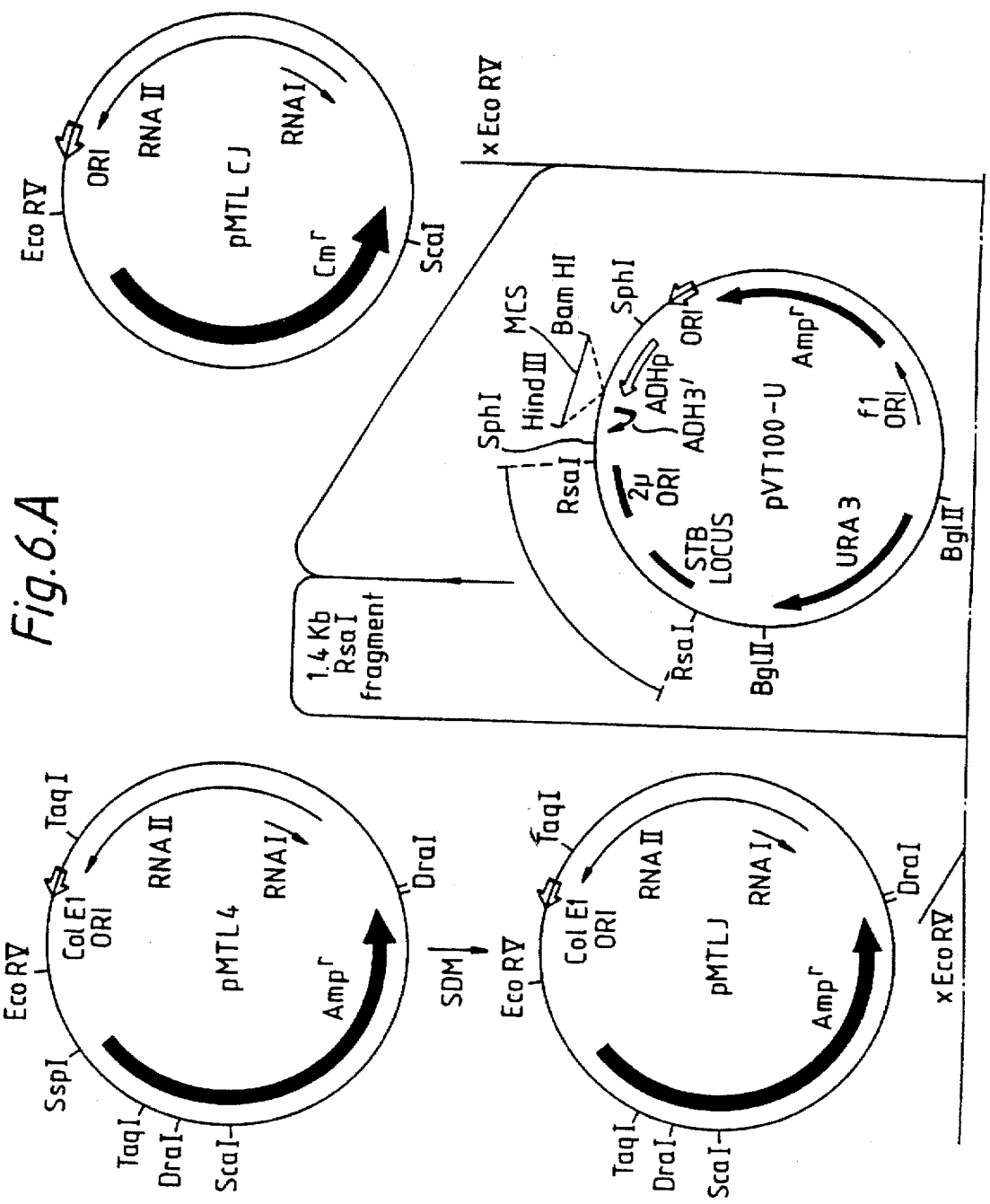
Fig. 6.A

BI-FUNCTIONAL EXPRESSION SYSTEM

The present invention relates to novel promoter DNA, particularly a novel expression system comprising DNA having a sequence containing transcriptional and translational signals that promote the over production of recombinant proteins both in bacterial hosts (eg., *Escherichia coli*) and yeasts (eg., *Saccharomyces cerevisiae*); and to a novel cloning method that allows the insertion of a heterologous gene into a vector or expression cassette directly at the authentic translational start point of a promoter, with no deleterious changes being made to either the native 5'-UTR of a vector promoter or to the codons of the inserted gene; allowing production of that promoter DNA. The design of the expression system lends itself to this unique strategy which allows heterologous genes to be directly cloned at a optimal position relative to the transcription/translation signals.

Particularly provided are expression cassettes comprising a sequence of the invention combined with a purpose built series of plasmids wherein the utility and efficiency of the resultant expression vectors can be demonstrated to over produce protein, particularly that of phenylalanine ammonia lyase (herein abbreviated to PAL), in *E. coli* and *S. cerevisiae* to levels hitherto unattainable.

BACKGROUND OF THE INVENTION

Although considerable progress has been made towards the development of expression systems for yeast (reviewed in Rose and Broach, 1990), the vectors lack the sophistication and versatility of their bacterial counterparts. Current vectors often contain many superfluous DNA sequences, which make them cumbersome and difficult to amplify and isolate in large quantities. The wealth of DNA present means that unique restriction sites are limited in number.

Yeast expression vectors are usually of the "sandwich" variety, whereby cloning sites are "sandwiched" between a homologous yeast promoter and transcriptional termination signals. The precise positioning of the cloning sites with respect to the authentic initiating codon (AUG) of the homologous yeast promoter represents something of a dilemma. If one chooses to place the cloning sites upstream to the AUG, then one inevitably disrupts the native 5'-untranslated region (5'-UTR) of the yeast promoter. Unavoidable insertion of heterologous untranslated sequence elements containing a high proportion of G residues, or elements creating secondary structures or containing the inserted AUG in a sub-optimal nucleotide context, can have catastrophic effects on expression levels, regardless of the strength of transcriptional activation signals (Donahue and Cigan, 1988; Baim and Sherman, 1988). For example, Bitter and Egan (1984) reported 10–15 fold lower expression levels of a Hepatitis B surface antigen (HBsAg) gene, fused to a yeast glyceraldehyde-3-phosphate (GPD) gene promoter, but utilising the native HBsAg 5' flanking region, compared to HBsAg fused to a GPD promoter and utilising the GPD 5' flanking region.

The alternative is to position the cloning sites immediately 3' to the authentic AUG of the yeast promoter. However, this has its own concomitant problems. Care must be taken that the fusion is "in frame", while the non-authentic amino terminus of the expressed protein may have unpredictable effects on its biological activity and antigenicity. These last two points render such fusion proteins unsuitable for use as a pharmaceutical without modification.

Preferably cloning is directly from the authentic AUG initiation codon. However, there has been no reported instance of a native yeast promoter with a usable restriction site encompassing its translational start point and the artificial creation of one would inevitably disrupt the start codon or its nucleotide context. The alternative is the lengthy and expensive procedure of chemically synthesizing an oligonucleotide "bridge" fragment that reaches from a convenient restriction site in the promoter 5' to the translational start to a site 3' to the ATG in the coding region to be expressed. Such a procedure is not applicable to a routine, versatile cloning strategy.

A further disadvantage with currently available yeast expression vectors is that as they employ homologous yeast promoters containing powerful transcriptional activating sequences and they do not direct the efficient transcription or translation in bacterial hosts, such as *E. coli* (Ratzkin and Carbon, 1977; Struhl, 1986). Similarly, bacterial derived transcriptional/translational signals are inefficiently utilised in *S. cerevisiae*, if at all. Comparative expression studies of heterologous genes in *E. coli* and *S. cerevisiae* therefore require the use of two separate vector systems.

DESCRIPTION OF THE INVENTION

A preferred aspect of the present invention describes how both the specificity and efficiency of a yeast promoter element, particularly that of *S. cerevisiae*, particularly that of PGK, can be changed to direct the high expression of heterologous genes in bacteria and yeasts.

A first aspect of the invention provides promoter DNA incorporating a structural gene starting position characterised in that the DNA has a unique SspI restriction site at the structural gene start position. A second aspect of the invention provides a novel cloning strategy ie. method, that allows the insertion of a heterologous gene into the expression cassette directly at the authentic translational start point of the promoter, with no deleterious changes being made to either the native 5'-UTR of the vector promoter or to the codons of the inserted gene; thus providing the promoter DNA of the first aspect.

A third aspect of the invention provides recombinant DNA comprising a yeast promoter sequence, particularly of *S. cerevisiae*, characterized in that the leader region of the promoter sequence is replaced with that of the replication protein 2 (REP2) gene (ORF C) of the yeast 2 μm plasmid (Hartley and Donelson, 1980). A preferred yeast promoter derived portion is that of the phosphoglycerate kinase (PGK) promoter and encompasses powerful upstream activating sequences (UAS) (Ogden et al., 1986), responsible for efficient transcription *S. cerevisiae*. The sequences necessary for efficient transcription in *E. coli* reside in the REP2 derived portion of the hybrid promoter. Sequences necessary for efficient translation, both in *S. cerevisiae* and *E. coli*, also reside in the REP2-derived portion of the promoter.

A fourth aspect of the invention provides the promoter hybrid of the invention incorporated into an expression "cassette", in which a copy of the lacZ' gene, containing the multiple cloning sites of pMTL23, is preceded by the promoter, and followed by tandemly arranged, yeast gene-derived, transcriptional terminators.

In the cloning method of the second aspect (illustrated in FIG. 1) promoter DNA incorporating a structural gene starting position eg. within an expression cassette, is modified using SDM by creating a unique SspI restriction site at a structural gene start position. The position of this created site is such that the triplet sequence, ATG, corresponding to the translational start codon of the structural gene becomes ATA within the SspI recognition site AATATT. The heterologous gene to be inserted is similarly modified. In this case the nucleotide triplet corresponding to the translational start codon (eg., AUG, GUG, or UUG) is changed to CAG, while the triplet immediately 5' is changed to CTG. These changes correspond to the creation of a PstI restriction site, CTG-CAG. The creation of the PstI, or equivalent site, can be conveniently performed simultaneously to isolation of the gene by utilising a mutagenic primer in a polymerase chain reaction (PCR) catalysed gene amplification procedure (Higuchi et al., 1988). The modified heterologous gene can be then digested with PstI restriction endonuclease and the 3' overhanging ends removed eg. by the 3' to 5' exonucleolytic activity of T4 DNA polymerase. The heterologous gene can then be excised using any of the restriction enzymes whose sites are present within the polylinker of the vector.

The net result of the actions of these DNA modifying enzymes is that the first base of the blunt-ended DNA fragment is the third nucleotide, "G", of its first codon. It is then ligated into the vector which has been digested previously with SspI and a restriction enzyme compatible with that used to excise the heterologous gene. Fusion of the vector promoter region (which ends in "AT") and heterologous gene (which begins in a "G") results in the recreation of the translational start, ATG.

The fourth aspect of the invention provides an expression system obtainable using the method of the invention such that overexpression of proteins is possible. A particular example of this is provided in the over expression of phenylalanine ammonia-lyase (PAL) gene from *Rhodosporidium toruloides* in both *E. coli* and *S. cerevisiae*. This is made possible by incorporating an expression cassette provided by the method into a purpose built, unique series of *S. cerevisiae/E. coli* shuttle plasmids. Preferably every component of these shuttle plasmids is extensively modified to reduce the presence of superfluous DNA in the final vectors and to eliminate nucleotide sequence motifs corresponding to the restriction enzyme recognition sites of use in the operation of the expression cassette. The levels of recombinant PAL attained in *S. cerevisiae* are significantly higher than that obtained using the PGK promoter alone. Whereas the PGK promoter alone fails to elicit the expression of PAL in *E. coli*, the levels of recombinant PAL obtained using the hybrid promoters are far in excess of those previously obtained using expression vectors designed for high expression in *E. coli*.

The DNA, cassettes, and organisms of the present invention will now be illustrated by reference to the following non-limiting Figures and Examples. Other variations falling within the scope of the invention will be apparent to those skilled in the art in the light of these.

BRIEF DESCRIPTION OF THE DRAWINGS

The invention will now be described in more detail with reference to the following sequence listing sequences and the accompanying drawings, in which:

FIGS. 6A and 6B: show the construction of pMTL 8000 and pMTL 8100 by inserting a 1.4 kb RsaI fragment from pVT100-U, containing the origin of replication and the STB locus from the 2 μm circle plasmid, into the EcoRV site of pMTLJ and pMTL CJ.

Figure 1:
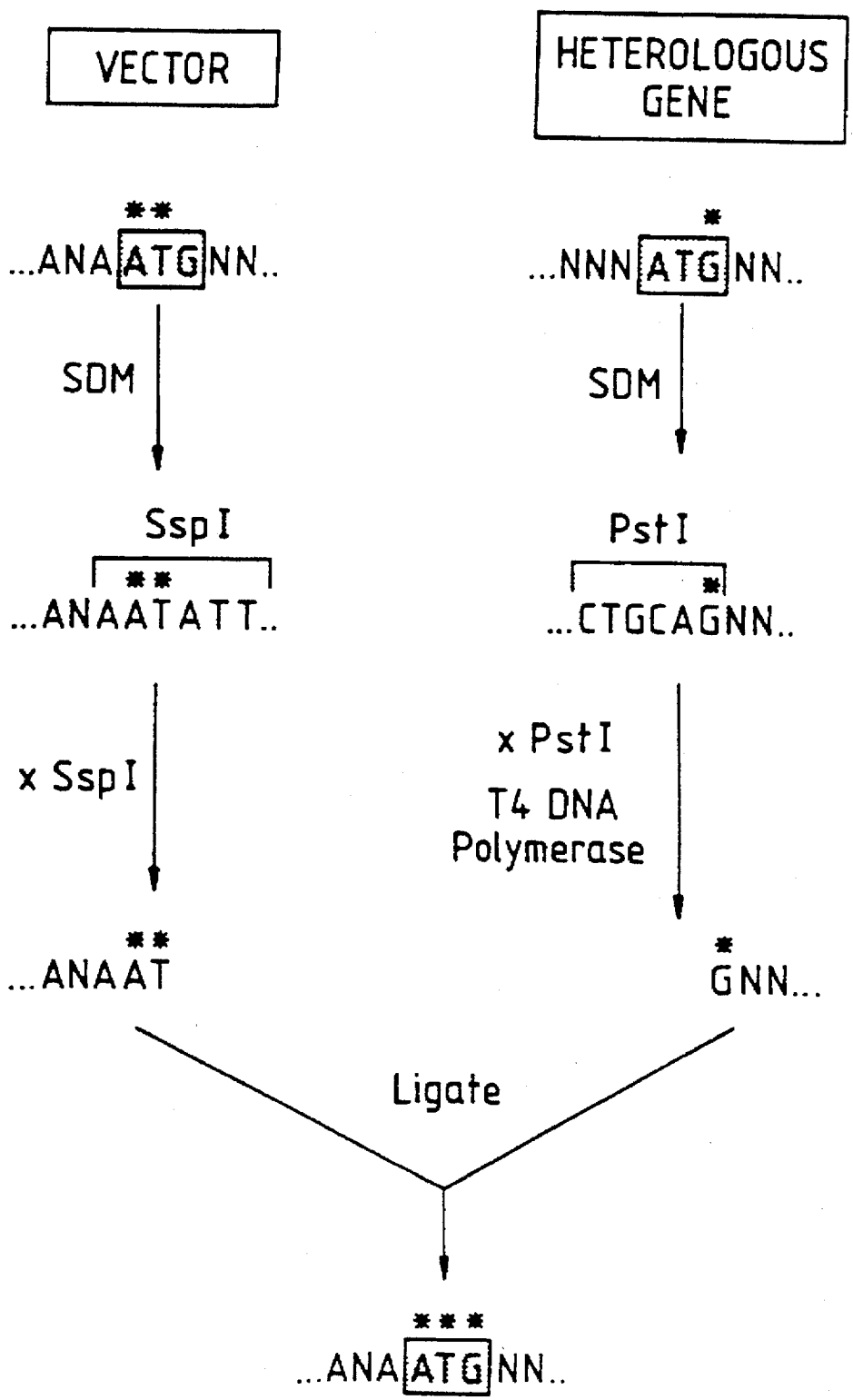
FIG. 1: shows the design of the novel cloning method which allows cloning to take place directly at the authentic translational start point of a promoter.
Figure 2:
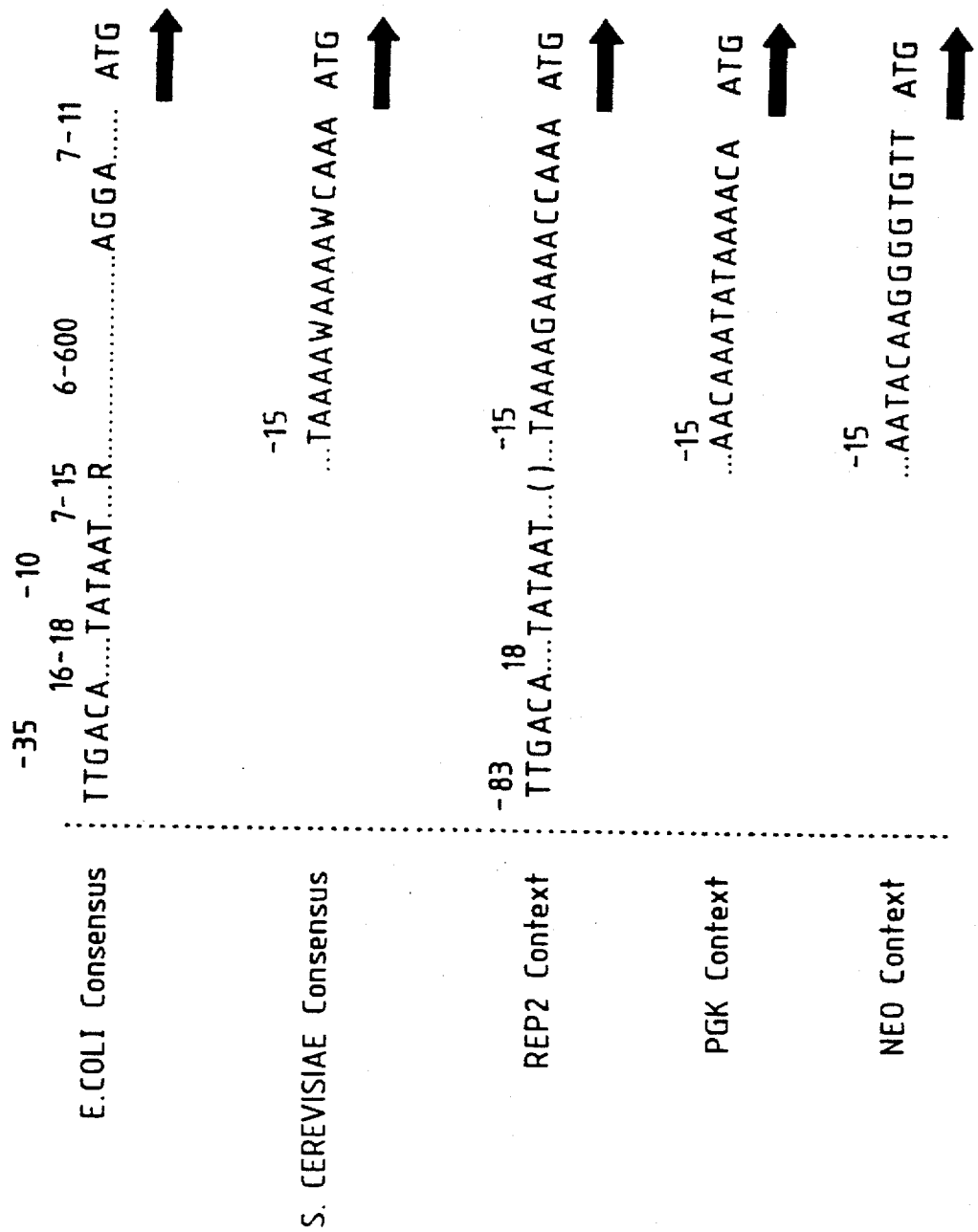
FIG. 2: shows a comparison of sequences found 5' to the translational start codon in REP2 and PGK, compared to a consensus yeast sequence, the sequence found 5' to the neo gene and a consensus procaryotic promoter sequence.
Figure 3:
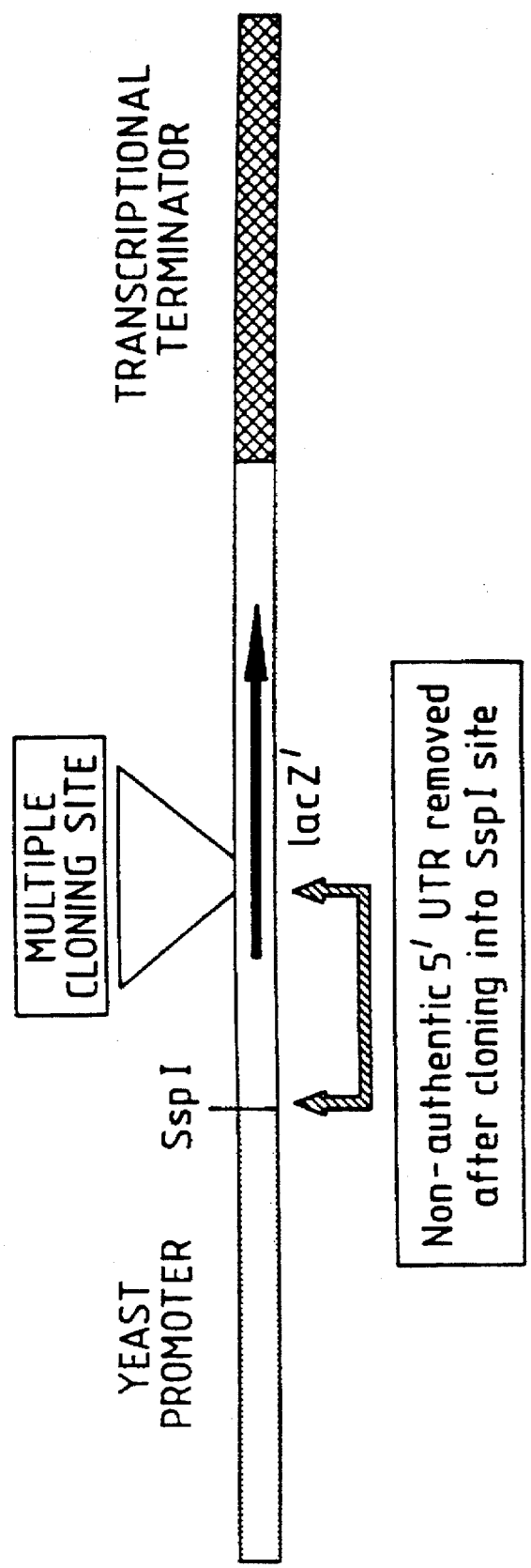
FIG. 3: shows how genes are inserted into the expression cassette using the SspI site.

SEQ ID No 1: shows the complete nucleotide sequence of a novel expression cassette (SEQ ID No 1) of the invention including a sequence comprising the PGK::REP2 promoter (bases 1-635; REP2 fragment consists of bases 547-635 of SEQ ID No 1).

SEQ ID No 2: is the complete nucleotide sequence of a comparative control cassette, containing the PGK promoter.

SEQ ID No 3: is the nucleotide sequence of plasmid pMTL8000.

SEQ ID No 4: is the nucleotide sequence of plasmid pMTL8100.

SEQ ID No 5: is the nucleotide sequence of the URA3-J and ura3-dJ (189=G) alleles used in the vector construction.

SEQ ID No 6: is the nucleotide sequence of the leu2-dJ allele used in vector construction.

In SEQ ID No 1, the original nucleotide source DNA sequences have been changed by SDM at the following points:

| Base 548-549 | was TT | now AC | Creates ClaI::AccI |
| Base 557 | was G | now T | |
| Base 580 | was G | now T | |
| Base 636-638 | was GTG | now ATT | |
| Base 1033-1035 | was TAA | now GTT | Creates HpaI::BglII |
| Base 1149 | was G | now C | Removes ClaI |
| Base 1223 | was T | now A | Removes SspI |
| Base 1484 | was G | now T | Removes AccI |

Restriction endonuclease sites are provided in regions of DNA as follows:

| Base 630-640 | SspI |
| Base 760-870 | NruI, StuI, XhoI, BglII, ClaI, SphI, NcoI, KpnI, SmaI, SstI, EcoRI, XbaI, HindIII, PstI, MluI, AccI, SalI, AatII, NdeI. BamHI. EcoRV, NaeI. |
| Base 1610-1619 | SphI |

Fusible ends were produced from the source DNA by ClaI and AccI for the fusion between base 546 and 547; by HpaI and BglII at for the fusion between base 1035 and 1036 and by HindIII and HincII for the fusion between base 1412 and 1413.

In SEQ ID No 2, the original nucleotide source DNA sequences have been changed by SDM at the following points:

| Base 3 | was C | now A | Creates EcoRI |
| Base 725-727 | was GAT | now AAG | Removes ClaI |
| Base 768-770 | was GTC | now ATT | Creates SspI |
| Base 1165-1167 | was TAA | now GTT | Creates HpaI |
| Base 1281 | was G | now C | Removes ClaI |

| Base 1356 | was T | now A | Removes SspI |
| Base 1616 | was G | now T | Removes AccI |

Restriction endonuclease sites are provided in regions of DNA as follows:

Base 1–10 EcoRI
Base 180–190 XmnI
Base 760–770 SspI
Base 890–1000 NruI, StuI, XhoI, BglII, ClaI, SphI, NcoI, KpnI, SmaI, SstI, EcoRI, XbaI, HindIII, PstI, MluI, AccI, SalI, AatII, NdeI, BamHI, EcoRV, NaeI.
Base 1740–1751 SphI Fusible ends were produced from the source DNA using HpaI and BglII for the fusion between 1167 and 1168; and using HindIII::HincII for the fusion between 1543 and 1544.

In SEQ ID No 3 derived from pVT100-U (bases 1–290 and 2295–3400) and pMTLJ (bases 291–2294), the original nucleotide source DNA sequences have been changed at the following points:

| Base 425 | was T | now C | Removes SspI |

Restriction endonuclease sites are provided in regions of DNA as follows:

| Base 1–10 | SspI |
| Base 1360–1370 | DraI |
| Base 2520–2530 | HpaI |

Fusable ends were produced from the source DNA using RsaI::EcoRV for the fusion between bases 290 and 291 and using EcoRV::RsaI for the fusion between bases 2294 and 2294.

In SEQ ID No 4 derived from pVT100-U (bases 1–290 and 1244–3249), pMTL4/CJ (bases 291–426 and 1214–2143) and pCM4 (bases 427–1213), the original nucleotide source sequences have ben changed at the following points:

| Base 676 | was A | now G | Removes EcoRI |
| Base 976 | was C | now A | Removes NcoI |
| Base 985 | was A | now G | Removes SspI |

Restriction endonuclease sites are provided in regions of DNA as follows:

| Base 1–10 | SspI |
| Base 2370–2380 | HpaI |

Fusible ends were produced from the using RsaI::EcoRV for the fusion between bases 290 and 291, SspI::BamHI for the fusion between bases 426 and 427, BamHI::DraI for the fusion between bases 1213 and 1214 and EcoRV::RsaI for the fusion between bases 2143 and 2144.

In SEQ ID No 5 the original nucleotide source sequence has been changed at the following points:

| Base 150 | was C | now G | Removes NdeI |
| Base 289 | was G | now C | Removes HpaI |
| Base 440 | was C | now G | Removes NcoI |
| Base 563 | was C | now T | Removes StuI |
| Base 1063 | was G | now C | Removes AccI |

Restriction endonuclease sites are thus absent from this sequence.

In SEQ ID No 6 the original nucleotide source sequence has been changed at the following points:

| Base 294 | was T | now C | Removes ClaI |
| Base 780 | was C | now T | Removes EcoRI |

Restriction endonuclease sites are provided in regions of DNA as follows:

| Base 380–390 | KpnI |

EXAMPLES

Example 1

Expression Cassettes. An example nucleotide composition of the expression cassette containing the essential elements of this invention is designated SEQ ID 1, and was formed by fusing DNA regions from PGK (base 1–546 and base 1036–1411), REP2 (base 547–635), lacZ' (base 636–1035) and ADH1 (base 1412–1619); base numbers are those in SEQ ID No 1 not source DNA. Prior to fusion, the sequence composition of each element was altered to varying extents using site-directed mutagenesis (SDM). In the majority of cases the changes were made either to eliminate a restriction enzyme recognition common to the polylinker region within lacZ', or to create a restriction recognition site to facilitate the construction of the cassette. To compare the advantages of the novel promoter element, a second cassette was constructed, which contained no REP2 derived nucleotides, to act as a control. The sequence composition of this control cassette is shown as SEQ ID No 2.

The expression cassettes consist of the E. coli lacZ' gene, containing the pMTL23 polylinker cloning sites (Chambers et al., 1988), sandwiched by nucleotide signals for transcriptional initiation and termination. The transcriptional initiation signals of the hybrid promoter are provided by a unique combination of sequences derived from the promoters of PGK and REP2. The upstream activating sequence (UAS) element and TATA-box are from the PGK promoter and are fused to the 86 nucleotides residing immediately 5' to the 2 μm plasmid REP2 gene. The REP2 promoter is constitutive in nature (Som et al., 1988), and not generally regarded as a "strong" yeast promoter.

Within the hybrid promoter, the REP2 region is also responsible for providing the expression cassette with promoter activity in E. coli. The region used contains sequence motifs which exactly correspond to those sequences necessary for transcription in procaryotes such as E. coli. Thus two hexanucleotide sequences are present, TTGACA and TATAAT, which exactly correspond to the consensus −35 and −10 boxes of E. coli promoters (Harley and Reynolds, 1987), and the spacing between them, 18 bp, is also consistent with a functional E. coli promoter. In addition, the AUG start codon of REP2 is preceded by the nucleotide motif -AGAA-.

The transcription initiation and termination signals flank unique restriction enzyme recognition sites into which heterologous genes may be inserted; with the exception of SspI, these sites form part of the lacZ' structural gene. Their location within the lacZ' gene allows the rapid detection of recombinant clones derived from the plasmid. The lacZ' gene encodes the alpha-peptide of β-galactosidase, such that when produced in *E. coli* hosts carrying the lacZ delta M15 mutation β-galactosidase leads to return of ability to metabolise the chromogenic substrate X-Gal and the production of blue colonies on agar medium supplemented with X-Gal. The insertion of heterologous DNA into the cloning sites of the expression cassette results in the inactivation of lacZ' and thus cells transformed with recombinant plasmid therefore produce colourless colonies on agar medium supplemented with X-Gal (Vieria and Messing, 1982).

The cassette is designed such that heterologous genes to be expressed are cloned using the SspI site and one of the recognition sites from within the polylinker. The SspI site (see list of sites in SEQ ID No 1 and 2 above) is located some 106 nucleotides 5' to the translational start of lacZ' and displacement of the DNA normally found between SspI and the polylinker within lacZ' results in recombinant plasmids which no longer confer a blue colouration on cells in the presence of X-Gal.

In the case of the PGK::REP2 promoter the ATA of the hexanucleotide sequence AATATT equates to the ATG start of the REP2 structural gene. In the case of the control expression cassette, the same triplet corresponds to the ATG start of the PGK structural gene. In both cases, when the cassettes are digested with SspI, the DNA is cleaved between the AT and A of the ATA triplet and a blunt-end is generated.

A DNA fragment carrying the gent to be expressed is then modified such that the first nucleotide of its blunt-ended. 5'-end is the "G" of the translational start codon of the structural gene. The 3'-end of this fragment may have any cohesive end compatible with those that can be generated by cleavage at the hexanucleotide recognition sites within lacZ'. Subsequent fusion of the 5' "G" nucleotide of the heterologous gene to the "AT" blunt-end of the cassette generated by SspI cleavage creates an ATG which is synonymous with both the translational start the heterologous gene and that of the structural genes from which the promoter elements were derived. ie., PGK in the case of the control cassette and REP2 in the case of the hybrid promoter.

The net result of the utilisation of this cloning strategy is that no changes are made to the nucleotides within the 5' untranslated region of the resultant mRNA, nor are any changes made to the codons of the gene being expressed. This would certainly not he true if a heterologous gene was merely inserted into the sites located solely in the polylinker region.

The method of choice used to allow the isolation of the heterologous gene as a blunt-ended fragment lacking the first two nucleotides of the translational start codon involves creating a recognition site for the restriction enzyme PstI at the start of the gene such that the terminal "G" of the created hexanucleotide sequence CTGCAG corresponds to the "G" of the genes translational start. The site created in the gene need not be PstI, but any site conforming to the consensus CNNNNG (where "N" is equivalent to, any nucleotide) which is cleaved by a restriction enzyme immediately before the "G" nucleotide to give a DNA terminus with a 3' overhang, ie., 3'-NNNN. Similarly, the recognition site used in the expression cassette need not be solely restricted to that of SspI, but can be any restriction site conforming to the consensus NATTAN (where "N" is equivalent to any nucleotide) which can be cleaved by a restriction enzyme between the two "T" nucleotides to give a blunt-end.

One potential problem with this cloning strategy occurs if the heterologous gene contains an internal PstI site. Two possible solutions are, firstly that the gene be inserted in a "two-step" cloning strategy utilising another internal site 5' to the problem PstI site. Secondly, an oligonucleotide can be designed such that its 5' end corresponds to the G residue of the ATG translational start point. If this oligonucleotide is used in a PCR catalysed reaction to isolate the gene of interest, then cleavage with PstI is unnecessary. However, the original "PstI" strategy is preferable to this latter strategy, since PCR products have frequently been shown to have slightly heterogeneous termini (Hemsley et al., 1989).

Example 2

Figure 4:
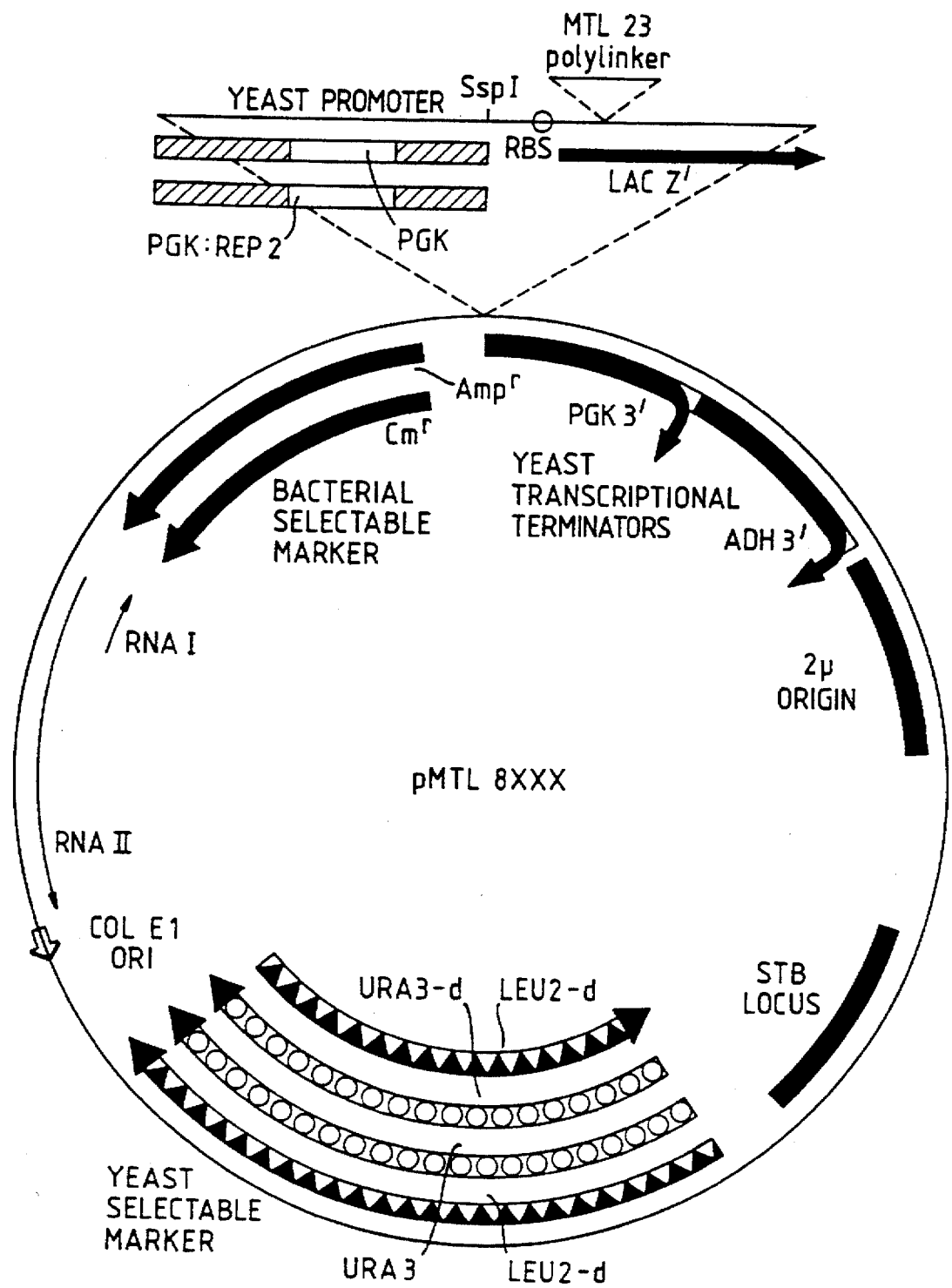
FIG. 4: shows an overview of the pMTL 8XXX vectors of the invention.

Preparation of Expression Vectors: A new series of vector backbones were constructed (see below) essentially being replication regions from the *E. coli* plasmid ColE1 and the yeast 2 μm plasmid. For selection in *E. coli* they carried either the bacterial cat or bla gene, conferring resistance to chloramphenicol (Cm) and ampicillin (Amp), respectively. The markers allowing selection in *S. cerevisiae* were either the LEU2 or URA3 gene, which convert appropriately deficient host strains to prototrophy. In the latter case, two alleles were constructed. Plasmids are shown in FIG. 4.

Regardless of the nature of the selectable marker, of bacterial or yeast origin, every vector contains a unique SspI site between the bacterial selectable marker and the 2 μm replication origin. It was into this site that the expression cassette and control cassette were inserted. The former was isolated as a 1.6 kb XmnI/SspI fragment, and the latter as a 1.75 kb EcoRI/SphI fragment. Both DNA fragments were blunt-ended by treatment with T4 DNA polymerase prior to their insertion into the SspI site. The orientation of insertion was such that lacZ' was counter transcribed relative to bla or cat.

Vector characteristics: CRM=chloramphenicol resistance marker. Gene markers transcribe away from STB but can transcribe toward it.

pMTL 8110: CRM, leu-dj gene marker, no cassette.

pMTL 8120: CRM, a defective *S. cerevisiae* URA3 gene and no cassette.

pMTL 8130: CRM, ura3-dj gene marker and no cassette.

pMTL 8131: CRM, ura3-dj gene marker and a cassette driven by the PGK promoter.

pMTL 8133: CRM, a defective *S. cerevisiae* URA3 gene and an expression cassette driven by the PGK:REP2 promoter.

pMTL 8140: CRM, leu2-dj gene marker and no cassette.

The vectors contain a minimum of 19 unique cloning sites in addition to the unique SspI sites. Non-unique sites are liven in Table 2.

Evaluation of the Expression Cassettes: The capabilities of the expression system were initially assessed using the neo gene of the transposon Tn903. It encodes aminoglycoside-3'-phosphotransferase type I (APH1), which confers resistance to the antibiotic kanamycin and its analogue C/418 (Haas and Dowding, 1975). The gene was available as a "Genblock (1.5 kb EcoRI fragment) from Pharmacia. This fragment was inserted into the EcoRI site of plasmid pUC8 to live plasmid pGENBLOCK. PCR was used to amplify a 1.11 kb fragment carrying the entire structural gene. During PCR the design of the oligonucleotide employed as the primer to the 5' end of the gene was such that a PstI recognition site was created. Specifically, the CAG of the created hexanucleotide sequence CTGCAG replaced the neo translational start codon.

The amplified fragment was digested with PstI and the overhanging 3' ends were removed by utilising the 3' to 5' exonuclease activity of T4 DNA polymerase. The fragment was then ligated with the pMTL 8111 and pMTL8113 expression vectors which had previously been digested with SspI and StuI and dephosphorylated. Colourless transformants were screened for the presence of the neo insert and the correct orientation by restriction analysis, and the plasmids obtained designated pKAN8111 and pKAN8113, respectively. Cells of *S. cerevisiae* strain AS33 carrying either plasmid were shown to be resistant to G418 at levels up to 3 mg/ml, indicative of extremely efficient expression of the neo gene. In contrast, only *E. coli* cells containing pKAN8113 were able to grow in the presence of CJ418 (at levels greater than 1 mg/ml). Lysates prepared from yeast carrying either plasmid cells were subjected to SDS-PAGE and the Comassie stained electro-phoretograms scanned with a Joyce-Loebell laser densitometer. A protein band equating to a size of 30,000 daltons was estimated to represent some 5% of the cell's soluble protein.

Primer Extension Analysis of *S. cerevisiae* mRNA: In order to ascertain the site(s) of transcriptional initiation within the two fusion promoters, mRNA was isolated from exponentially growing YEPD cultures of *S. cerevisiae* AS33 containing pKAN8111 and pKAN8113. A 25 bp oligonucleotide primer was synthesised, complementary to the coding strand at +53 to +77 within the neo coding region, and purified to homogeneity. It was not necessary to consider wild-type chromosomal transcription, since the neo gene does not occur chromosomally. Primer extension was performed and the products compared with end-labelled DNA sequence reactions primed with the same oligo-nucleotide primer.

The results demonstrated that the mRNA transcriptional start point (tsp) of the PGK promoter of pKAN8111 maps to nucleotide at −42. This is one nucleotide further from the AUG than that reported by Van den Heuvel et al. (1989) and 2 nucleotides further than that determined by Mellor et al. (1985). Over 90% of transcription from the PGK:REP2 promoter of pKAN8113 appeared to initiate at nt −87 at a G residue. Thus, REP2 promoter tsp site plays no role in transcription, rather factors within the PGK portion of the promoter direct the position and pattern of RNA initiation. Rathjen and Mellor (1990) have shown that initiation in PGK is reliant on two cis-acting sequences, the TATA element at nt −152 and a sequence, 5'-ACAGATCA-3', located immediately 5' to the site of RNA called the "determinator". In the PGK:REP2 promoter, however, the first "C" of the determinator has been deleted without any apparent effect.

Over Production of PAL in *E. coli* and *S. cerevisiae*: A PstI site was introduced over the authentic translational start point of a PAL cDNA clone from *Rhodosporidium toruloides* (Anson et al., 1986; Anson et el., 1987; Rasmussen and Orum, 1991) using PCR-mediated SDM (Higuchi et al..1988); an XbaI site lying 115 bp downstream from the PAL UAG termination codon. The PAL gene was excised as a PstI (blunt)/XbaI fragment and cloned into SspI/XbaI cut pMTL 8131 and pMTL 8133 to generate pPAL 8131 and pPAL 8133 respectively. The expression of PAL in *S. cerevisiae* strain AS33 is shown in Table 3. The lower expression levels obtained when cells are grown in rich selective media probably reflect a drop in plasmid copy number (Rose and Broach, 1990), although a decline in promoter activity and/or increase in mRNA turnover cannot be discounted.

Figure 5:
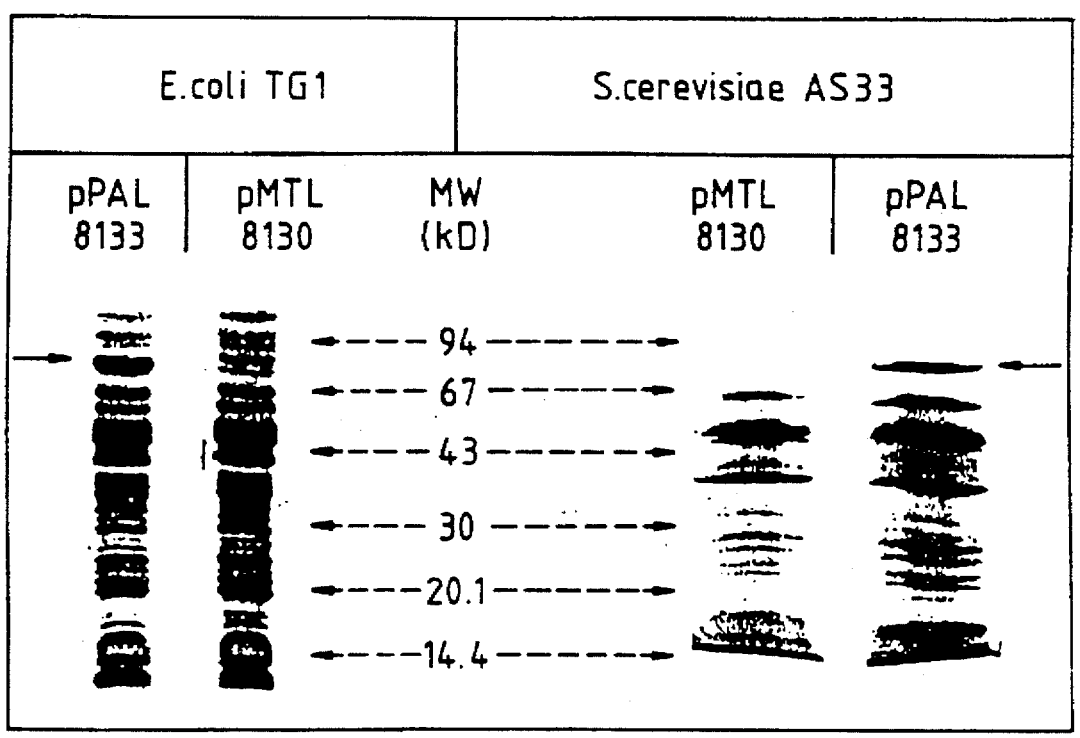
FIG. 5: shows an SDS-PAGE electrophoretogram of lysates derived from microbial cells producing recombinant PAL.

The crude cell-free extracts were analysed by PAGE (FIG. 5) and a band corresponding to a protein of approximate MW 75 kD, which is present only in the strain carrying pPAL 8133. was detected. This corresponds to the molecular weight of the PAL monomer. The gel was scanned with a laser densitometer (Joyce-Loebell) which calculated that this band constitutes approximately 9% of total soluble cell protein. This correlates well with the figure obtained by comparing the specific activity of purified PAL at 30° C. with the assay data. This would indicate that the vast majority of the recombinant PAL is produced in an active form.

PAL expression levels in *E. coli* TG1 (Table 3) confirmed the finding that the PGK:REP2 promoter is highly active in *E. coli*, whilst the native PGK promoter is inactive. Deletion of part of the putative "−35" region resulted in partial loss of activity of this promoter in *E. coli* (data not shown), indicating that it is indeed these signals which are activating transcription in *E. coli*. Quantitative scanning of polyacrylamide gels indicated PAL expression levels to be of the order of 10% total soluble cell protein.

MATERIALS AND METHODS: A.1 Strains, Plasmids, Transformation and Media.

The *S. cerevisiae* strain AS33 (a, his3-11, his3-15, leu2-3, leu2-112, ura3-251, ura3-373, trp1) was used throughout. Yeast were transformed by electroporation (Becker and Guarente, 1991) and transformants selected by their ability to complement the appropriate auxotrophic allale. *E. coli* strain TG1 (Carter et al., 1985) was used as host for all DNA manipulations and bacterial expression studies. Plasmid pVT100-U (Vernet et al., 1987) was a kind gift from Dr. T. Vernet and plasmid pCM4 (Close and Rodriguez, 1982) obtained from Pharmacia. All DNA manipulations were carried out essentially as described in Sambrook et al. (1989). Polymerase chain reaction (PCR) was carried out on a programmable thermal cycler using Taq DNA polymerase (Amplitaq, Perkin-Elmer Cetus). DNA sequencing was based on the modified chain termination procedure described by Tabor and Richardson (1987). Oligos were synthesised using an Applied Biosystems 380A DNA synthesiser.

Site-directed mutagenesis (SDM) was performed by a number of techniques. Initially, mutants were created using a derivation of the method described by Carter et al., (1985). Subsequently, SDM was performed by a method based on that described by Kunkel (1985).

Latter mutagenesis experiments were carried out using a novel coupled-primer method for SDM. Essentially, a PCR product was generated using kinased oligos, one of which contained the mutagenic mis-match, whilst the other was located at a point on the target plasmid such that a restriction site, which was unique in the plasmid, lay between the two primers. This PCR product was mixed with an equimolar amount of target plasmid DNA, which had been passaged through an *E. coli* dut ung strain, and linearised at the unique restriction site. The DNA mixture was denatured at 65° C. for 5 min in denaturing buffer (0.2M NaOH, 0.2 mM EDTA), before neutralisation (2M NH$_4$Ac, pH 4.5) and subsequent ethanol precipitation. The DNA was redissolved in annealing buffer (20 mM Tris-HCl, pH 7.4; 2 mM MgCl$_2$, 50 mM NaCl) and annealed for 15 min at 37° C. Extension reactions were at 37° C. for 1 hr in a buffer containing 1× TM buffer, 5 mM DTT, 500 μM dNTPs, 250 μM rATP, 2 units T4 DNA ligase and 10 units Sequenase. Aliquots of this reaction were then transformed into *E. coli* TG1.

Typical mutagenesis frequencies were in the region of 30%. This technique obviates the need for sub-cloning into specialised vectors or the use of repair-deficient strains. Assay for PAL Activity: PAL levels in cell-free extracts were assayed by the method of Abell and Shen (1987). The production of cinnamic acid can be monitored spectrophotometrically at 290 nm. 0.67 ml distilled water, 0.17 ml 6× assay buffer (500 mM Tris-HCl pH 8.5) and 0.17 ml L-phenylalanine (50 mM in 100 mM Tris-HCl pH 8.5) were combined in a 1 ml cuvette (Hughes and Hughes Ltd., UV range). The cuvette and its contents were pre-warmed to 30° C. and placed in a Perkin-Elmer Lambda 2 Spectrophotometer. 25 µl of crude cell extract was added and the absorbance at 290 nm was monitored for 30 seconds at 30° C.

One unit of enzyme was defined as the amount catalysing formation of 1 µmol cinnamic acid per minute under the assay conditions used. The molar absorption coefficient for cinnimate at 290 nm, 30° C., pH 8.5 ($E_{290}$) was taken as 9×10³ liter/mol/cm (Abell and Shen, 1987). The level of PAL activity can then be calculated as follows:

$$IU/ml = \frac{deltaA290 \times 10^3 \times \text{Dilution Factor}}{E \frac{290}{1000} \times \mu l \text{ of sample}}$$

Protein concentrations were determined by the method of Bradford (1976).

Derivation of the Expression Cassette: The initial stages involved in construction were common to each cassette. Two mutagenic oligonucleotides were employed to PCR amplify a 410 bp fragment of pMTL23 encompassing lacZ' and the lac po region (Chambers et al., 1988). The resultant modified fragment possessed a SspI site at position −106 (relative to the lacZ' translational start codon) and a HpaI site at nucleotide position +293 (relative to the lacZ' start codon). The transcriptional termination signals of the PGK were cloned from S. cerevisiae strain LL20 chromosomal DNA as a 373 bp BglII/HindIII fragment into M13mt120 (Chambers et al., 1988). The restriction enzyme recognition sites for ClaI and SspI were eliminated by SDM, and the DNA reisolated as a BglII/HindIII fragment. The 3'end of the ADH1 locus was sub-cloned from pVT100-U (Vernet et al., 1987) as a 335 bp SphI/HindIII fragment into similarly cleaved M13mp18. An AccI recognition site removed by SDM, and the region carrying the desired transcriptional termination signals reisolated as a 206 bp HincIII/SphI fragment. The three DNA fragments specifying lacZ', the PGK transcriptional terminator and the ADH1 transcriptional terminator were then fused, by ligation with DNA ligase, in the order and orientation shown in SEQ ID No 1 and 2. Prior to fusion, the staggered ends of the DNA fragment encompassing the PGK transcriptional terminator (those generated by cleavage with BglII and HindIII) were blunt-ended by treatment with T4 DNA polymerase.

To complete the control cassette, a 3.1 kb HindIII fragment carrying the PGK gene of S. cerevisiae strain LL20 was inserted into M13mp8 and SDM employed to create restriction recognition sites for EcoRI and SspI. In the case of the SspI recognition site, its position was such that the ATG triplet corresponding to the translational start codon of the PGK structural gene became the ATA of the SspI site, AATATT. A 766 bp fragment encompassing the transcriptional signals of PGK was then isolated from the resultant mutagenic M13 clone, M13PGK-J, following cleavage with EcoRI and SspI, and ligated to the 999 bp SspI/SphI fragment composed of lacZ'::PGK::ADH1, such that the SspI recognition site was retained.

To complete the expression cassette containing the hybrid promoter, a 1.8 kb HindIII fragment (nucleotides 4621 to 92 of the sequence of Hartley and Donelson, 1980) carrying the promoter of the 2 µm plasmid REP2 gene was subcloned into the equivalent site of M13mp8. Recognition sites for the restriction enzymes AccI and SspI were then created in the sequence by SDM. This was achieved by changing the hexanucleotide sequences GTTGTT and AATGGA (respective nucleotide positions 5288 to 5283 and 5199 to 5194; Hartley and Donelson, 1980) to GTCGAC and AATATT, respectively. Additionally, two "G" nucleotides (positions 557 and 580 in SEQ ID No 2) were both changed to "T". The recombinant plasmid obtained was designated M13REP2-J. An additional recognition site for the restriction enzyme ClaI was also created within the PGK derived region of M13PGK-J. The changes made are detailed above in the section on features of SEQ ID No 2, at positions 725 and 727. The transcriptional signals of PGK were then isolated as a 540 bp XmnI/ClaI fragment, and ligated to a 90 bp AccI/SspI fragment isolated from M13REP2-J, such that fusion occurred between the compatible ClaI and AccI derived DNA sticky ends. The resultant 630 bp fragment was then ligated to the 999 kb SspI/SphI fragment composed of lacZ'::PGK::ADH1, such that the SspI recognition site was retained.

Nucleotide sequence analysis of the various components of the constructed cassettes indicated the presence of nucleotide differences to previously published sequences, presumably a consequence of strain variation. Specifically, several base differences were observed between the transcriptional initiation and termination regions of the PGK gene used here and that determined by Hitzeman et al. (1982). By reference to SEQ ID No 2, the Hitzeman et al. (1982) sequence has 5 "A" nucleotides rather than the 4 beginning at position 760, lacks the "G" at position 729, has an extra "A" between nucleotides 1399 and 1400, and an extra "T" nucleotides between position 1493 and 1494. Similarly, the "A" nucleotide at position 1663 was found to be a "G" in the ADH1 gene determined by Bennetzen and Hall (1985).

Two additional nucleotide mutations occurred during the construction of the expression cassette containing the hybrid promoter, around the junction point between the PGK promoter and the REP2 leader region. Thus, a "C" nucleotide base has been deleted from between positions 538 and 539 in SEQ ID No 1 (the "C" at position 716 in SEQ ID No 2), and the nucleotide base at position 543 has become an "A", rather than the "C" found in the equivalent position of the strain LL20 PGK promoter (position 721 of SEQ ID No 2).

Example 3

Figure 6B:
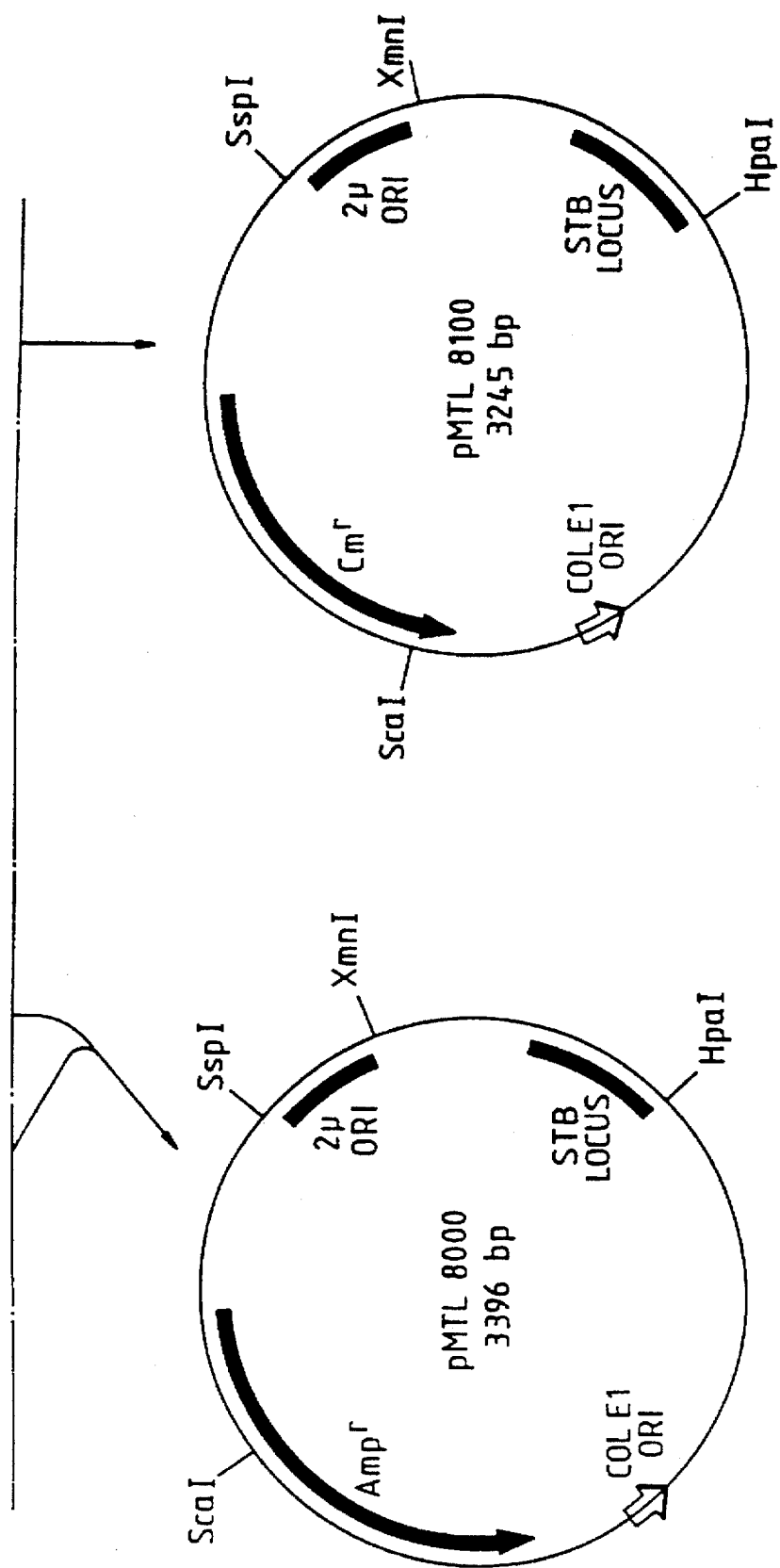

Derivation of E. coli/S. cerevisiae Shuttle Vectors:

Provision of E. coli maintenance and replication functions: the first stage in the construction of the new E. coli/S. cerevisiae vectors was to combine the replicative functions of an E. coli plasmid with that of a S. cerevisiae plasmid. Two basic vectors were made, pMTL8000 and pMTL8100. As shown in FIG. 6, both were constructed by isolating a 1.4 kb RsaI, which encompassed the origin of replication and STB locus of the 2 µm plasmid, from plasmid pVT100-U (Vernet et al., 1987), and inserting it into the unique EcoRV sites of either pMTLJ or pMTLCJ to give pMTL8000 or pMTL8100, respectively.

Figure 7A:
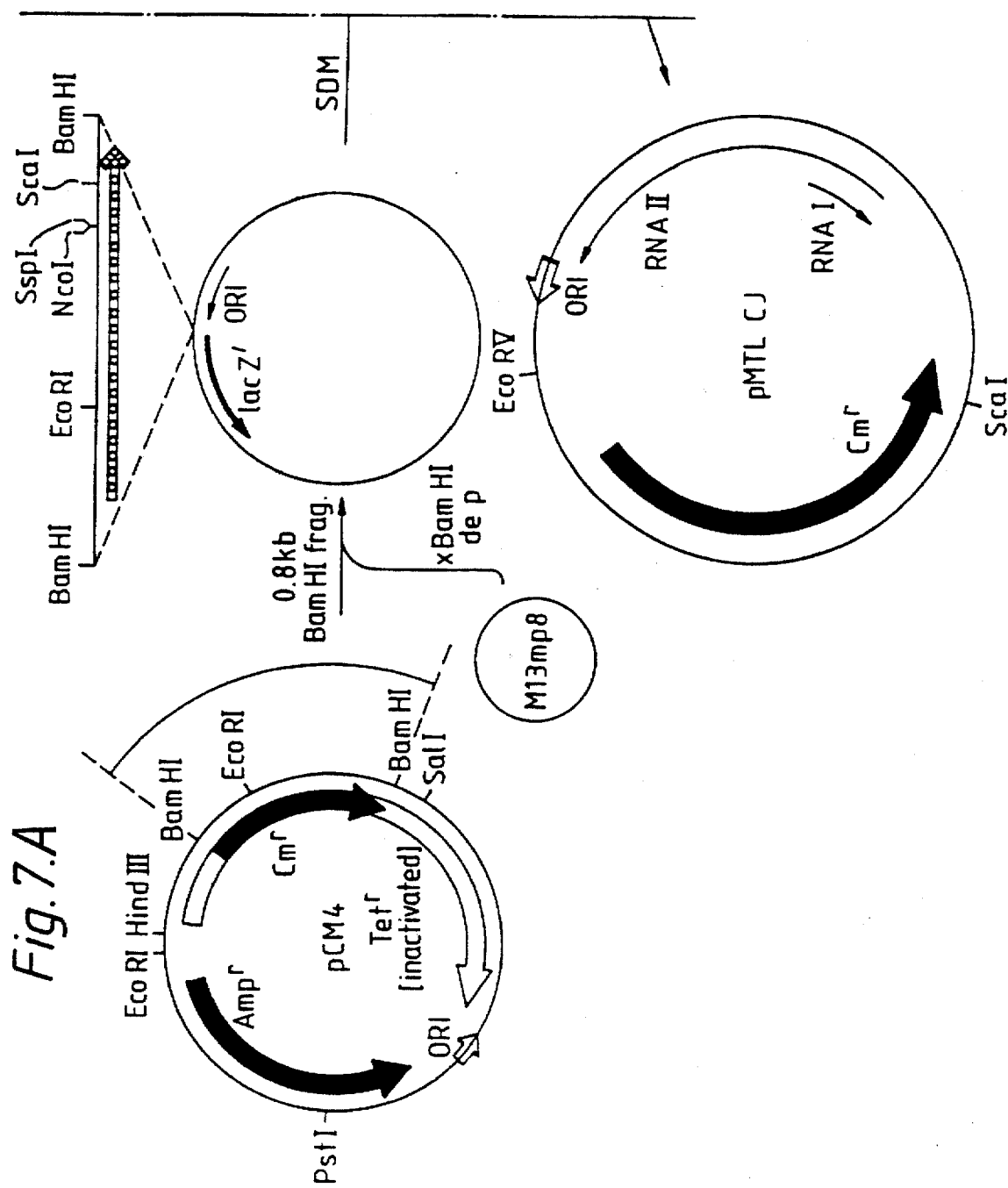
FIGS. 7A and 7B: show the construction of pMTLCJ by replacing the bla gene of pMTL4 with the cat gene of pCM4, modified by SDM-mediated removal of EcoRI, NcoI and SspI restriction sites.
Figure 7B:
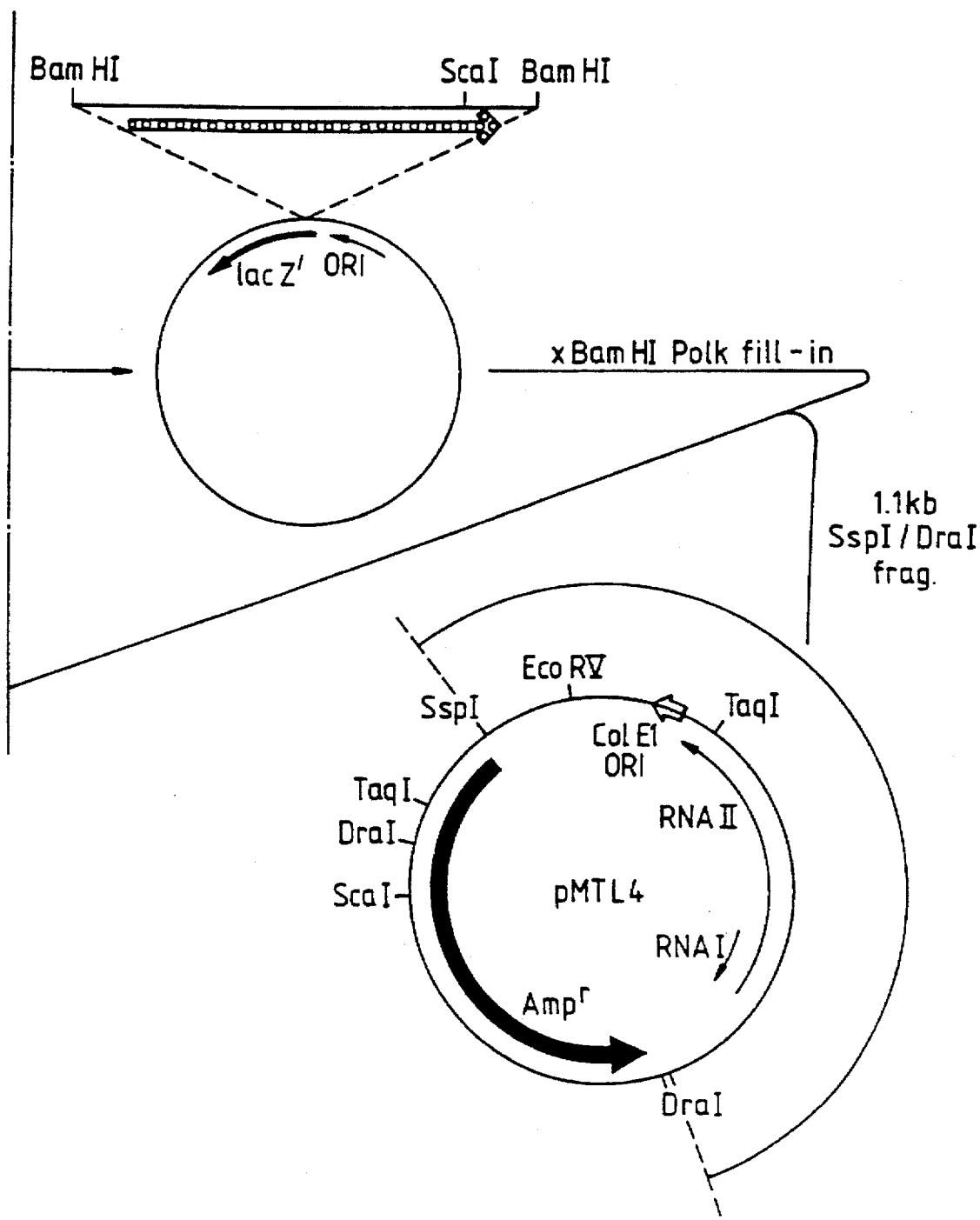

Plasmid pMTLJ was derived from pMTL4 (Chambers et al., 1988), by eliminating the recognition site for the restriction enzyme SspI using the plasmid SDM method. The steps involved in the derivation of pMTLCJ are shown in FIG. 7. Essentially, a 0.8 kb BamHI fragment, encoding cat, was excised from plasmid pCM4 (Close and Rodriguez, 1982) and inserted into the BamHI site of M13mp8. The ssDNA prepared from the resultant recombinant was then used as a template in successive SDM experiments to eliminate restriction enzyme recognition sites for EcoRI, NcoI and SspI from the cat structural gene. ds DNA of the mutated M13 recombinant was then prepared, the modified cat gene excised as a 0.8 kb BamHI fragment, blunt-ended by treatment with DNA polymerase I Klenow fragment and ligated to a 1.1 kb SspI/DraI fragment encompassing the replication region of plasmid pMTL4 to give pMTLCJ.

The nucleotide sequences of pMTL8000 and pMTL8100 are shown as SEQ ID No 3 and 4. The 2 μm replication region resides between nucleotides 3154 to 3376 of pMTL8000 and 3003 to 3225 of pMTL8100. The STB locus is between nucleotides 2526 to 2817 of pMTL8000 and between 2375 and 2666 of pMTL8100. The bla structural gene begins at nucleotide 444 of pMTL8000 and ends at position 1304. The cat structural gene of pMTL8100 begins at nucleotide 461 and ends at position 1117. In both cases, the amino acid sequence of the encoded proteins are shown below the first nucleotide of the corresponding codon in the single letter code. The ColE1 origin of replication lies at nucleotides 2063–2068 and 1912–1917 in pMTL8000 and pMTL8100, respectively.

Provision of markers for plasmid selection in *S. cerevisiae*: The basic backbone of the vector series was completed by inserting DNA sequence elements into pMTL8000 and pMTL8100 which allowed direct selection of the described plasmid series in appropriate auxotrophic *S. cerevisiae* host strains. Two different selective markers were employed.

Firstly, a 1.17 kb BglII fragment containing the *S. cerevisiae* URA3 gene was sub-cloned from pVT100-U into the BamHI site of M13mp8. The ssDNA prepared from the resultant recombinant was then used as a template in successive SDM experiments designed to eliminate unique restriction enzyme recognition sites for NdeI, NcoI, and StuI, and two AccI restriction sites. This modified gene was designated the URA3-J allele. The complete sequence of the DNA fragment actually inserted into the eventual expression vectors (see below) is shown as SEQ ID No 5. The URA3 structural gene initiates at nucleotide 234 and terminates at nucleotide 1034. The amino acid sequence of the encoded protein is shown in the single letter code below the first nucleotide of the corresponding codon.

In addition to the standard URA3 selectable marker, a promoterless version, ura3-d was also created. SDM was employed to create a HpaI site at nt −47 (relative to the AUG start codon) in the URA3-J allele. This equates to changing the "C" nucleotide at position 189 to a "G". Subsequent excision of the gene by cleaving with HpaI at this point removes all sequences necessary for activation of the $URA_3$ gene (Roy et al., 1990), whilst retaining the major transcriptional start points at nt −38 and −33 (Rose and Botstein, 1983). It was anticipated that plasmids endowed with ura3-d would possess elevated plasmid copy number under selective conditions, as observed with plasmids carrying an equivalent promoterless LEU2 gene, leu2-d (Ecrhart and Hollenberg, 1983).

The second selectable marker used was the LEU2 gene. This was sub-cloned as a 1.46 kb SspI fragment from pMA300 (Montiel et al., 1984) into the SmaI site of pUC8. This fragment lacks the sequences mapped as the UAS of LEU2 at −201 to −187 (Tu and Casadaban, 1990), and disrupts the sequence upstream from LEU2 which codes for a putative regulatory peptide (Andreadis et al., 1982). However, it retains the TATA-like AT-rich sequence between bases −118 to −111 that has been proposed as a site for the yeast TATA-binding factor TFIID (Tu and Casadaban, 1990). The recombinant, pUC8-derived plasmid carrying LEU2 was used as a template in SDM experiments to remove the recognition sites for the restriction enzymes ClaI and EcoRI. In the sequence shown as SEQ ID No 5 the URA3 structural gene initiates at nucleotide 234 and terminates at nucleotide 1034. The amino acid sequence of the encoded protein is shown in the single letter code below the first nucleotide of the corresponding codon.

To insert the three alleles URA3-J, ura3-dJ and leu2-dJ into the unique pMTL 8000 and pMTL 8100, each allele was excised from the appropriate plasmid and converted, where necessary, to a blunt-ended DNA fragment. In the case of URA3-J, plasmid pURA3-J was cleaved with AccI (cleaving at a site within the pUC8 polylinker region) and SmaI (cleaving at a SmaI site residing some 79 nucleotides 3' to the translational stop codon of URA3) and the released c. 1.1 kb fragment carrying URA3 treated with T4 DNA polymerase. The exact sequence of the blunt-ended fragment generated is shown in SEQ ID No 5. A c.0.92 kb blunt-ended fragment carrying the ura3-dJ allele was obtained by cleaving plasmid pURA3-dJ with HpaI and SmaI.

The nucleotide sequence of the fragment obtained exactly corresponds to the sequence shown in SEQ ID No 5 between nucleotide 192 and 1115, inclusive. Plasmid pLEU2-dJ was cleaved with EcoRI (at the recognition site within the pUC8 polylinker region) and AccI (at a recognition site located 100 nucleotides 3' to the translational stop of URA3. The exact sequence of the blunt-ended fragment generated is shown in SEQ ID No 6.

All three isolated fragments carrying URA3-J, ura3-dJ and leu2-dJ were inserted into the unique HpaI site of both pMTL8000 and pMTL8100. With one exception, all the recombinant plasmids obtained no longer contained HpaI sites. The exceptions were the pMTL8000 and pMTL8100 derivatives carrying ura3-dJ, where the HpaI site is retained at the junction point lying 5' end to the gene. To avoid compromising the segregational stability of the plasmids by potential read-through from the selective markers into STB (Murray and Cesareni, 1986), clones were orientated such that the yeast selective markers transcribed away from the STB locus. For comparative purposes, a plasmid containing the leu2-dJ allele transcribing towards STB were also constructed.

Physical Characterisation of Constructed Vectors: Before proceeding to insert the expression cassette into the vector series, the basic backbone vectors were assessed with regard to their stability (segregational and structural) and copy number.

Measurement of plasmid segregational stability in *S. cerevisiae*: Plasmid segregational stability was estimated using methodology described by Spalding and Tuite (1989). This involved following the loss of a plasmid-encoded phenotypic marker over a number of generations under non-selective conditions. The results are presented in Table 1. All plasmids exhibited a greater degree of segregational stability than that of the well characterised *S. cerevisiae* cloning vector YEp24 (Botstein et al., 1979).

Measurement of structural stability: The structural stability of plasmids in *S. cerevisiae* was assessed by transforming each plasmid into strain AS33, growing cells fop approximately 30 generations under selective conditions, and then transferring each plasmid back to *E. coli* by the procedure of Hoffman and Winston (1987). Plasmid DNA was then prepared, by the method of Holmes and Quigley (1981), from the resultant *E. coli* transformants and subjected to restriction enzyme analysis. The restriction patterns obtained with all such plasmids isolated from *E. coli*, using the enzymes SspI and EcoRV, was identical to that of the CsCl-purified DNA originally transformed into strain AS33.

Estimation of Dismid CODV number: Plasmid copy number determination was based on the non-isotopic technique of Futcher and Cox (1984). Approximately 5 μg of total yeast DNA was digested simultaneously with EcoRI and EcoRV. Following agerose gel electrophoresis, a negative image of the restriction "spectrum" was scanned using a laser densitometer (Joyce-Loebell). The intensity of the band corresponding to plasmid DNA was compared with that of the 2.8 kb rDNA EcoRI fragment. The rDNA was assumed to be present at 140 tandem copies (Philipssen et al., 1991). Plasmid copy number was then calculated as follows:

$$\text{Plasmid Copy Number} = \frac{\text{Area under plasmid peak}}{\text{Area under rDNA 2.8 kb peak}} \times \frac{2.8 \times 140}{\text{plasmid size (kb)}}$$

Using this method, the copy numbers of the basic plasmid vectors in S. cerevisiae were compared to previously characterised high copy number (pMA3a; Spalding and Tuite, 1989) and low copy number (YEp24; Botstein et al., 1979) plasmids. The results in Table 1 confirm that low copy number (pMTL 8120) and high copy number (pMTL 8110, 8130 and 8140) versions, of the vectors described in the present invention, have been constructed.

TABLE 1

Segregational stability and copy number analysis of the pMTL 81X0 series of vectors.

| Plasmid | Cells contg.* Plasmid (%) | Plasmid loss/ cell div($10^{-2}$) | Average copy number/cell |
|---|---|---|---|
| pMTL 8110 | 84.5 | 0.842 | 111 |
| pMTL 8120 | 77.5 | 1.174 | 50 |
| pMTL 8130 | 82.0 | 0.992 | 151 |
| pMTL 8140 | 85.5 | 0.783 | 106 |
| YEp24 (URA3) | 76.0 | 1.372 | 48 |
| pMA3a (leu2-d) | ND | ND | 106 |

*After 20 generations of non-selective exponential growth.

Segregational stability was performed using methodology described by Spalding and Tuite (1989) and is an average of two or more independent experiments. Copy number data is for cells grown in minimal media and is based on the assumption that all cells contain plasmid under these conditions. The selective marker present within each vector is shown in brackets. R=reverse orientation. ND=not determined.

TABLE 2

Non-unique restriction sites present within the polylinkers of the pMTL 8XXX series of vectors.

| Marker | PGK | No Promoter | PGK:REP2 |
|---|---|---|---|
| leu2-d | EcoRV.Kpn1.Sst1 | EcoRV.Kpn1 | EcoRV.Kpn1.Sst1 |
| URA3 | EcoRV | EcoRV | EcoRV |
| ura3-d | EcoRV.Sst1 | EcoRV | EcoRV.Sst1 |
| leu2-d | EcoRV.Kpn1.Sst1 | EcoRV.Kpn1 | EcoRV.Kpn1.Sst1 |

TABLE 3

Expression of PAL in S. cerevisiae AS33 and E.coli TG1.
Figures refer to units $\times 10^{-2}$/mg soluble protein. At least three separate assays were performed for each sample and the maximum error range is indicated. ND = not determined. PAL = presence of PAL gene.

| Strain and growth phase | pMTL 8130 | pPAL 8133 | pPAL 8131 |
|---|---|---|---|
| S.cerevis' AS33 Minimal media Stationary | 0 | 35.5 ± 2 | 18.1 ± 2 |
| S.cerevis' AS33 YEPD Early exponent' | 0 | 37.8 ± 3 | ND |
| S.cerevis' AS33 YEPD Stationary | 0 | 16.5 ± 1 | 8.5 ± 0.7 |
| E. coli TG1 2 × YT Stationary | 0 | 35.2 ± 2 | 0 |

REFERENCES:
Abell, C., and Shen, R. (1987). Meth. Enzymol. 142, 242–248.
Andreadis, A. et al (1984). J. Biol. Chem. 259, 8059–8062.
Anson, J., Gilbert, H., Oram, J, and Minton, N. (1986). GB App 8621626
Anson, J., Gilbert, H., Oram, J, and Minton, N. (1987). Gene 58, 189–199.
Baim, S., and Sherman, F. (1988). Mol. Cell. Biol. 8, 1591–1601.
Becker, D., and Guarente, L. (1991). Meth. Enzymol, 194, 182–187.
Bitter, G., and Egan, K. (1984) Gene 32, 263–274.
Botstein, D. et al (1979) Gene 8, 17–24.
Bradford, M. (1976). J. Anal. Biochem. 72, 248–254.
Carter, P. et al (1985). Oligonucleotide site-directed mutagenesis in M13. (Anglian Biotechnology Ltd., Colchester, Essex).
Chambers, S. et al (1988a). Gene 68, 139–149.
Chambers, S. et al (1988b). Appl. Micro. and Biotech. 29, 572–578.
Close, T., and Rodriguez, R. (1982). Gene 20, 305–316.
Donahue, T., and Cigan, A. (1988). Mol. Cell. Biol. 8, 2955–2963.
Futcher, A., and Cox, B. (1984). J. Bacteriol. 157, 283–290.
Haas, M., and Dowding, J. (1975) Meth. Enzymol. 43, 611–628.
Harley, C., and Reynolds, R. (1987). Nucl. Acids Res. 15, 2343–2361.
Hartley, J., and Donelson, J. (1980). Nature 286, 860–865.
Hemsley, A., et al (1989) Nucl. Acids Res. 17, 6545–6551.
Higuchi, R. et al (1988). Nucl. Acids Res. 16, 7351–7367.
Hitzeman, R. et al (1982). Nucl. Acids Res. 10, 7791–7808.
Hoffman, C., and Winston, F. (1987). Gene 57, 267–272.
Holmes, D., and Quigley, M. (1981). Anal. Biochem. 114, 193–197.
Kunkel, T. (1985). Proc. Natl. Acad. Sci. USA 82, 488–492.
Mellor, J. et al (1985). Gene 33, 215–226.
Montiel, J. et al (1984). Nucl. Acids Res. 12, 1049–1058.
Murray, J., and Cesareni, G. (1986). EMBO J 5, 3391–3399.
Ogden, J. et al (1986). Mol. Cell. Biol. 6, 4335–4343.

Orum, H. and Rasmussen, O. (1992). Appl. Microbiol. Biotechnol. 36,745–748.

Rasmussen, O. and Orum, H. (1991). DNA Sequence J. 1, 207–211.

Ratzkin, B., and Carbon, J. (1977) Proc. Natl. Acad. Sci. USA 74, 487–491.

Rose, A., and Broach, J. (1990). Meth. Enzymol. 185, 234–279.

Rose, M., and Botstein, D. (1983). J. Mol. Biol. 170, 883–904.

Roy, A. et al (1990). Yeast 6 (special issue), 324.

Sambrook, J. et al (1989). Molecular cloning—a laboratory manual. Second edition. (Cold Spring Harbour Laboratory, Cold Spring Harbour, N.Y.).

Spalding, A., and Tuite, M. (1989). J. Gen. Microbiol. 135, 1037–1045.

Struhl, K. (1986). J. Mol. Biol. 191, 221–229.

Tabor, S., and Richardson, C. (1987). Proc. Natl. Acad. Sci. USA 84,4767–4771.

Tu, H., and Casadaban, M. (1990). Nucl. Acids Res. 18, 3923–3931.

Vernet, T. et al. (1987). Gene 52, 225–233.

Vieria, J., and Messing, J. (1982). Gene 19, 259–268.

We claim:

1. A recombinant DNA comprising a yeast promoter sequence of SEQ ID NO: 1 wherein the leader region promoter sequence is replaced with leader sequence of the replication protein 2 (REP2) gene (ORF C) of the yeast 2 μm plasmid, and wherein the yeast promoter derived portion is that of the phosphoglycerate kinase (PGK) promoter.

2. A recombinant DNA as claimed in claim 1 wherein the upstream activating sequence element and TATA-box are those as found in the PGK promoter.

3. A recombinant DNA as claimed in claim 2 wherein the UAS team activating sequence element and TATA-box are fused to the 86 nucleotides residing immediately 5' to the 2 µm plasmid REP2 gene.

4. A recombinant DNA comprising a sequence of bases 1 to 635 of SEQ ID 1.

5. A recombinant DNA as claimed in claim 1 wherein the yeast promoter incorporates a structural gene start position which provides a unique SspI restriction site.

6. An expression cassette comprising recombinant DNA as claimed in claim 1 wherein it further includes a copy of the lacZ' gene, containing the multiple cloning sites of pMTL23, preceded by the promoter DNA of claim 1, and followed by tandemly arranged, yeast gene-derived, transcriptional terminators.

7. An expression cassette comprising a DNA sequence SEQ ID 1.

8. An *E. coli* or *S. cerevisiae* shuttle plasmid comprising an expression cassette as claimed in claim 6.

9. Recombinant DNA, an expression cassette, or a plasmid as claimed in claim 1 further comprising a gene coding for phenylalanine ammonia lyase.

10. A method for producing recombinant DNA as claimed in claim 5 wherein the unique SspI restriction site at the structural gene start position is provided by altering the ATG codon corresponding to the authentic structural gene translational start position to the ATA triplet within the SspI recognition site AATATT.

11. A method for inserting a heterologous gene at the structural gene start position of recombinant DNA as claimed in claim 5 comprising the steps of:

(a) altering the heterologous gene such that its 5' end corresponds to the G nucleotide of its the start codon ATG, (b) digesting the recombinant DNA with SspI such that its 3' end corresponds to the AT nucleotides of the structural gene start position, and (c) ligating the 3' end of the recombinant DNA to the 5' end of the heterologous gene such as to regenerate a translational start codon, ATG.

12. A method for inserting a heterologous gene as claimed in claim 11 wherein the G nucleotide at the 5' end of the heterologous gene is provided by altering ATG codon triplet corresponding to the heterologous gene translational start codon to CAG and altering the triplet immediately 5' to the codon to CTG in order to provide a PstI restriction site, CTGCAG, and digesting the altered heterologous gene with PstI restriction endonuclease.

13. A method for inserting a heterologous gene as claimed in claim 12 wherein the PstI restriction site is provided simultaneously to isolating the heterologous gene by use of a mutagenic primer comprising a PstI restriction site in a Polymerase Chain Reaction catalysed gene amplification procedure.

14. A method for inserting a heterologous gene as claimed in claim 11 wherein the G nucleotide at the 5' end of the heterologous gene is provided simultaneously to isolating the heterologous gene by use of a mutagenic primer comprising a 5' G nucleotide in a Polymerase Chain Reaction catalysed gene amplification procedure.

15. A method for cloning a heterologous gene into an expression cassette as claimed in claim 7 wherein the 3' end of the heterologous gene is prepared using one or more of the restriction enzymes whose sites are present within the pMTL23 polylinker and the heterologous DNA is then ligated into the cassette which has been digested previously with SspI and a restriction enzyme compatible with that used to prepare the heterologous gene.

16. A method of producing protein in a yeast or bacterial host organism comprising cloning a gene coding for the protein into an expression cassette as claimed in claim 15 and inserting the expression cassette into the host.

17. A method as claimed in claim 11 wherein the gene codes for phenylanaline ammonia lyase.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 1619 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Saccharomyces cerevisiae ( i x ) FEATURE:
( A ) NAME/KEY: misc_recomb
( B ) LOCATION: 546..547

( i x ) FEATURE:
( A ) NAME/KEY: misc_recomb
( B ) LOCATION: 635..636

( i x ) FEATURE:
( A ) NAME/KEY: misc_recomb
( B ) LOCATION: 1035..1036

( i x ) FEATURE:
( A ) NAME/KEY: misc_recomb
( B ) LOCATION: 1411..1412

( i x ) FEATURE:
( A ) NAME/KEY: misc_feature
( B ) LOCATION: 550..555

( i x ) FEATURE:
( A ) NAME/KEY: misc_feature
( B ) LOCATION: 574..579

( i x ) FEATURE:
( A ) NAME/KEY: misc_feature
( B ) LOCATION: 668..673

( i x ) FEATURE:
( A ) NAME/KEY: misc_feature
( B ) LOCATION: 692..697

( x i ) SEQUENCE DESCRIPTION: SEQ ID NO: 1:

```
GAATTGTTTC CCTCCTTCTT GAATTGATGT TACCCTCATA AAGCACGTGG CCTCTTATCG      60

AGAAAGAAAT TACCGTCGCT CGTGATTTGT TTGCAAAAAG AACAAACTG AAAAAACCCA     120

GACACGCTCG ACTTCCTGTC TTCCTATTGA TTGCAGCTTC CAATTTCGTC ACACAACAAG    180
```

-continued

| | | | | | | |
|---|---|---|---|---|---|---|
| GTCCTAGCGA | CGGCTCACAG | GTTTTGTAAC | AAGCAATCGA | AGGTTCTGGA | ATGGCGGGAA | 240 |
| AGGGTTTAGT | ACCACATGCT | ATGATGCCCA | CTGTGATCTC | CAGAGCAAAG | TTCGTTCGAT | 300 |
| CGTACTGTTA | CTCTCTCTCT | TTCAAACAGA | ATTGTCCGAA | TCGTGTGACA | ACAACAGCCT | 360 |
| GTTCTCACAC | ACTCTTTTCT | TCTAACCAAG | GGGGTGGTTT | AGTTAGTAG | AACCTCGTGA | 420 |
| AACTTACATT | TACATATATA | TAAACTTGCA | TAAATTGGTC | AATGCAAGAA | ATACATATTT | 480 |
| GGTCTTTTCT | AATTCGTAGT | TTTTCAAGTT | CTTAGATGCT | TTCTTTTCT | CTTTTTTAAG | 540 |
| ATAATCGACT | TGACATTTGA | TCTGCACAGA | TTTTATAATT | TAATAAGCAA | GAATACATTA | 600 |
| TCAAACGAAC | AATACTGGTA | AAAGAAACC | AAAATATTAG | TTAGCTCACT | CATTAGGCAC | 660 |
| CCCAGGCTTT | ACACTTTATG | CTTCCGGCTC | GTATGTTGTG | TGGAATTGTG | AGCGGATAAC | 720 |
| AATTTCACAC | AGGAAACAGC | TATGACCATG | ATTACGCCAA | GCTCGCGAGG | CCTCGAGATC | 780 |
| TATCGATGCA | TGCCATGGTA | CCCGGGAGCT | CGAATTCTAG | AAGCTTCTGC | AGACGCGTCG | 840 |
| ACGTCATATG | GATCCGATAT | CGCCGGCAAT | TCACTGGCCG | TCGTTTTACA | ACGTCGTGAC | 900 |
| TGGGAAAACC | CTGGCGTTAC | CCAACTTAAT | CGCCTTGCAG | CACATCCCCC | TTTCGCCAGC | 960 |
| TGGCGTAATA | GCGAAGAGGC | CCGCACCGAT | CGCCCTTCCC | AACAGTTGCG | TAGCCTGAAT | 1020 |
| GGCGAATGGC | GCGTTGATCT | CCCATGTCTC | TACTGGTGGT | GGTGCTTCTT | TGGAATTATT | 1080 |
| GGAAGGTAAG | GAATTGCCAG | GTGTTGCTTT | CTTATCCGAA | AAGAAATAAA | TTGAATTGAA | 1140 |
| TTGAAATCCA | TAGATCAATT | TTTTCTTTT | CTCTTTCCCC | ATCCTTTACG | CTAAAATAAT | 1200 |
| AGTTTATTTT | ATTTTTTGAA | TATATTTTAT | TTATATACGT | ATATATAGAC | TATTATTTAC | 1260 |
| TTTTAATGAT | TATTAAGATT | TTTATTAAAA | AAAAATTCGT | CCCTCTTTTT | AATGCCTTTT | 1320 |
| ATGCAGTTTT | TTTTCCCAT | TCGATATTTC | TATGTTCGGG | TTCAGCGTAT | TTTAAGTTTA | 1380 |
| ATAACTCGAA | AATTCTGCGT | TCGTTAAAGC | TGACACTTCT | AAATAAGCGA | ATTTCTTATG | 1440 |
| ATTTATGATT | TTTATTATTA | AATAAGTTAT | AAAAAAAATA | AGTTTATACA | AATTTTAAAG | 1500 |
| TGACTCTTAG | GTTTTAAAAC | GAAAATTCTT | ATTCTTGAGT | AACTCTTTCC | TGTAGGTCAG | 1560 |
| GTTGCTTTCT | CAGGTATAGC | ATGAGGTCGC | TCTTATTGAC | CACACCTCTA | CCGGCATGC | 1619 |

( 2 ) INFORMATION FOR SEQ ID NO: 2:

( i ) SEQUENCE CHARACTERISTICS:
        ( A ) LENGTH: 1754 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Saccharomyces cerevisiae ( i x ) FEATURE:
        ( A ) NAME/KEY: misc_recomb
        ( B ) LOCATION: 546..547

( i x ) FEATURE:
        ( A ) NAME/KEY: misc_recomb
        ( B ) LOCATION: 635..636

( i x ) FEATURE:
        ( A ) NAME/KEY: misc_recomb
        ( B ) LOCATION: 1035..1036

( i x ) FEATURE:
        ( A ) NAME/KEY: misc_recomb (B) LOCATION: 1411..1412

(xi) SEQUENCE DESCRIPTION: SEQ ID NO: 2:

```
GAATTCAACT CAAGACGCAC AGATATTATA ACATCTGCAT AATAGGCATT TGCAAGAATT      60
ACTCGTGAGT AAGGAAAGAG TGAGGAACTA TCGCATACCT GCATTTAAAG ATGCCGATTT     120
GGGCGCGAAT CCTTTATTTT GGCTTCACCC TCATACTATT ATCAGGGCCA GAAAAAGGAA     180
GTGTTTCCCT CCTTCTTGAA TTGATGTTAC CCTCATAAAG CACGTGGCCT CTTATCGAGA     240
AAGAAATTAC CGTCGCTCGT GATTTGTTTG CAAAAGAAC AAAACTGAAA AAACCCAGAC      300
ACGCTCGACT TCCTGTCTTC CTATTGATTG CAGCTTCCAA TTTCGTCACA CAACAAGGTC     360
CTAGCGACGG CTCACAGGTT TTGTAACAAG CAATCGAAGG TTCTGGAATG GCGGGAAAGG     420
GTTAGTACC ACATGCTATG ATGCCCACTG TGATCTCCAG AGCAAAGTTC GTTCGATCGT      480
ACTGTTACTC TCTCTCTTTC AAACAGAATT GTCCGAATCG TGTGACAACA ACAGCCTGTT     540
CTCACACACT CTTTCTTCT AACCAAGGGG GTGGTTTAGT TTAGTAGAAC CTCGTGAAAC      600
TTACATTTAC ATATATATAA ACTTGCATAA ATTGGTCAAT GCAAGAAATA CATATTTGGT     660
CTTTTCTAAT TCGTAGTTTT TCAAGTTCTT AGATGCTTTC TTTTTCTCTT TTTTACAGAT     720
CATCAAGGGA AGTAATTATC TACTTTTTAC AACAAATATA AAACAATATT AGTTAGCTCA     780
CTCATTAGGC ACCCCAGGCT TTACACTTTA TGCTTCCGGC TCGTATGTTG TGTGGAATTG     840
TGAGCGGATA ACAATTTCAC ACAGGAAACA GCTATGACCA TGATTACGCC AAGCTCGCGA     900
GGCCTCGAGA TCTATCGATG CATGCCATGG TACCCGGGAG CTCGAATTCT AGAAGCTTCT     960
GCAGACGCGT CGACGTCATA TGGATCCGAT ATCGCCGGCA ATTCACTGGC CGTCGTTTTA    1020
CAACGTCGTG ACTGGGAAAA CCCTGGCGTT ACCCAACTTA ATCGCCTTGC AGCACATCCC    1080
CCTTTCGCCA GCTGGCGTAA TAGCGAAGAG GCCCGCACCG ATCGCCCTTC CAACAGTTG     1140
CGTAGCCTGA ATGGCGAATG GCGCGTTGAT CTCCATGTC TCTACTGGTG GTGGTGCTTC     1200
TTTGGAATTA TTGGAAGGTA AGGAATTGCC AGGTGTTGCT TTCTTATCCG AAAAGAAATA    1260
AATTGAATTG AATTGAAATC CATAGATCAA TTTTTTTCTT TTCTCTTTCC CCATCCTTTA    1320
CGCTAAAATA ATAGTTTATT TTATTTTTG AATATATTTT ATTTATATAC GTATATATAG     1380
ACTATTATTT ACTTTTAATG ATTATTAAGA TTTTTATTAA AAAAAAATTC GTCCCTCTTT    1440
TTAATGCCTT TTATGCAGTT TTTTTTTCCC ATTCGATATT TCTATGTTCG GGTTCAGCGT    1500
ATTTTAAGTT TAATAACTCG AAAATTCTGC GTTCGTTAAA GCTGACACTT CTAAATAAGC    1560
GAATTTCTTA TGATTTATGA TTTTTATTAT TAAATAAGTT ATAAAAAAAA TAAGTTTATA    1620
CAAATTTTAA AGTGACTCTT AGGTTTTAAA ACGAAAATTC TTATTCTTGA GTAACTCCTC    1680
TTTCCTGTAG GTCAGGTTGC TTTCTCAGGT ATAGCATGAG GTCGCTCTTA TTGACCACAC    1740
CTCTACCGGC ATGC                                                     1754
```

(2) INFORMATION FOR SEQ ID NO: 3:

(i) SEQUENCE CHARACTERISTICS:
      (A) LENGTH: 3400 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iii) ANTI-SENSE: NO (vi) ORIGINAL SOURCE:

( A ) ORGANISM: Saccharomyces cerevisiae ( i x ) FEATURE:
  ( A ) NAME/KEY: misc_recomb
  ( B ) LOCATION: 290..291

( i x ) FEATURE:
  ( A ) NAME/KEY: misc_recomb
  ( B ) LOCATION: 2294..2295

( x i ) SEQUENCE DESCRIPTION: SEQ ID NO: 3:

| | | | | | |
|---|---|---|---|---|---|
| AATATTTTAG | TAGCTCGTTA | CAGTCCGGTG | CGTTTTTGGT | TTTTTGAAAG | TGCGTCTTCA | 60 |
| GAGCGCTTTT | GGTTTTCAAA | AGCGCTCTGA | AGTTCCTATA | CTTTCTAGCT | AGAGAATAGG | 120 |
| AACTTCGGAA | TAGGAACTTC | AAAGCGTTTC | CGAAAACGAG | CGCTTCCGAA | AATGCAACGC | 180 |
| GAGCTGCGCA | CATACAGCTC | ACTGTTCACG | TCGCACCTAT | ATCTGCGTGT | TGCCTGTATA | 240 |
| TATATATACA | TGAGAAGAAC | GGCATAGTGC | GTGTTTATGC | TTAAATGCGT | ATCCCGCAAG | 300 |
| AGGCCCGGCA | GTCAGGTGGC | ACTTTTCGGG | GAAATGTGCG | CGGAACCCCT | ATTTGTTTAT | 360 |
| TTTTCTAAAT | ACATTCAAAT | ATGTATCCGC | TCATGAGACA | ATAACCCTGA | TAAATGCTTC | 420 |
| AATACTATTG | AAAAGGAAG | AGTATGAGTA | TTCAACATTT | CCGTGTCGCC | CTTATTCCCT | 480 |
| TTTTTGCGGC | ATTTTGCCTT | CCTGTTTTTG | CTCACCCAGA | AACGCTGGTG | AAAGTAAAAG | 540 |
| ATGCTGAAGA | TCAGTTGGGT | GCACGAGTGG | GTTACATCGA | ACTGGATCTC | AACAGCGGTA | 600 |
| AGATCCTTGA | GAGTTTTCGC | CCCGAAGAAC | GTTTTCCAAT | GATGAGCACT | TTTAAAGTTC | 660 |
| TGCTATGTGG | CGCGGTATTA | TCCCGTATTG | ACGCCGGGCA | AGAGCAACTC | GGTCGCCGCA | 720 |
| TACACTATTC | TCAGAATGAC | TTGGTTGAGT | ACTCACCAGT | CACAGAAAAG | CATCTTACGG | 780 |
| ATGGCATGAC | AGTAAGAGAA | TTATGCAGTG | CTGCCATAAC | CATGAGTGAT | AACACTGCGG | 840 |
| CCAACTTACT | TCTGACAACG | ATCGGAGGAC | CGAAGGAGCT | AACCGCTTTT | TTGCACAACA | 900 |
| TGGGGATCA | TGTAACTCGC | CTTGATCGTT | GGGAACCGGA | GCTGAATGAA | GCCATACCAA | 960 |
| ACGACGAGCG | TGACACCACG | ATGCCTGTAG | CAATGGCAAC | AACGTTGCGC | AAACTATTAA | 1020 |
| CTGGCGAACT | ACTTACTCTA | GCTTCCCGGC | AACAATTAAT | AGACTGGATG | GAGGCGGATA | 1080 |
| AAGTTGCAGG | ACCACTTCTG | CGCTCGGCCC | TTCCGGCTGG | CTGGTTTATT | GCTGATAAAT | 1140 |
| CTGGAGCCGG | TGAGCGTGGG | TCTCGCGGTA | TCATTGCAGC | ACTGGGGCCA | GATGGTAAGC | 1200 |
| CCTCCCGTAT | CGTAGTTATC | TACACGACGG | GGAGTCAGGC | AACTATGGAT | GAACGAAATA | 1260 |
| GACAGATCGC | TGAGATAGGT | GCCTCACTGA | TTAAGCATTG | GTAACTGTCA | GACCAAGTTT | 1320 |
| ACTCATATAT | ACTTTAGATT | GATTTAAAAC | TTCATTTTTA | ATTTAAAAGG | ATCTAGGTGA | 1380 |
| AGATCCTTTT | TGATAATCTC | ATGACCAAAA | TCCCTTAACG | TGAGTTTTCG | TTCCACTGAG | 1440 |
| CGTCAGACCC | CGTAGAAAAG | ATCAAAGGAT | CTTCTTGAGA | TCCTTTTTTT | CTGCGCGTAA | 1500 |
| TCTGCTGCTT | GCAAACAAAA | AAACCACCGC | TACCAGCGGT | GGTTTGTTTG | CCGGATCAAG | 1560 |
| AGCTACCAAC | TCTTTTTCCG | AAGGTAACTG | GCTTCAGCAG | AGCGCAGATA | CCAAATACTG | 1620 |
| TTCTTCTAGT | GTAGCCGTAG | TTAGGCCACC | ACTTCAAGAA | CTCTGTAGCA | CCGCCTACAT | 1680 |
| ACCTCGCTCT | GCTAATCCTG | TTACCAGTGG | CTGCTGCCAG | TGGCGATAAG | TCGTGTCTTA | 1740 |
| CCGGGTTGGA | CTCAAGACGA | TAGTTACCGG | ATAAGGCGCA | GCGGTCGGGC | TGAACGGGGG | 1800 |
| GTTCGTGCAC | ACAGCCCAGC | TTGGAGCGAA | CGACCTACAC | CGAACTGAGA | TACCTACAGC | 1860 |
| GTGAGCATTG | AGAAAGCGCC | ACGCTTCCCG | AAGGGAGAAA | GGCGGACAGG | TATCCGGTAA | 1920 |
| GCGGCAGGGT | CGGAACAGGA | GAGCGCACGA | GGGAGCTTCC | AGGGGGAAAC | GCCTGGTATC | 1980 |
| TTTATAGTCC | TGTCGGGTTT | CGCCACCTCT | GACTTGAGCG | TCGATTTTTG | TGATGCTCGT | 2040 |

| | | | | | | |
|---|---|---|---|---|---|---|
|CAGGGGGGCG|GAGCCTATGG|AAAAACGCCA|GCAACGCGGC|CTTTTTACGG|TTCCTGGCCT|2100|
|TTTGCTGGCC|TTTTGCTCAC|ATGTTCTTTC|CTGCGTTATC|CCCTGATTCT|GTGGATAACC|2160|
|GTATTACCGC|CTTTGAGTGA|GCTGATACCG|CTCGCCGCAG|CCGAACGACC|GAGCGCAGCG|2220|
|AGTCAGTGAG|CGAGGAAGCG|GAAGAGCGCT|AGCAGCACGC|CATAGTGACT|GGCGATGCTG|2280|
|TCGGAATGGA|CGATACTTGT|TACCCATCAT|TGAATTTTGA|ACATCCGAAC|CTGGGAGTTT|2340|
|TCCCTGAAAC|AGATAGTATA|TTTGAACCTG|TATAATAATA|TATAGTCTAG|CGCTTTACGG|2400|
|AAGACAATGT|ATGTATTTCG|GTTCCTGGAG|AAACTATTGC|ATCTATTGCA|TAGGTAATCT|2460|
|TGCACGTCGC|ATCCCGGTT|CATTTCTGC|GTTCCATCT|TGCACTTCAA|TAGCATATCT|2520|
|TTGTTAACGA|AGCATCTGTG|CTTCATTTG|TAGAACAAAA|ATGCAACGCG|AGAGCGCTAA|2580|
|TTTTCAAAC|AAAGAATCTG|AGCTGCATTT|TTACAGAACA|GAAATGCAAC|GCGAAAGCGC|2640|
|TATTTACCA|ACGAAGAATC|TGTGCTTCAT|TTTGTAAAA|CAAAAATGCA|ACGCGAGAGC|2700|
|GCTAATTTTT|CAAACAAAGA|ATCTGAGCTG|CATTTTACA|GAACAGAAAT|GCAACGCGAG|2760|
|AGCGCTATTT|TACCAACAAA|GAATCTATAC|TTCTTTTTG|TTCTACAAAA|ATGCATCCCG|2820|
|AGAGCGCTAT|TTTCTAACA|AAGCATCTTA|GATTACTTTT|TTTCTCCTTT|GTGCGCTCTA|2880|
|TAATGCAGTC|TCTTGATAAC|TTTTGCACT|GTAGGTCCGT|TAAGGTTAGA|AGAAGGCTAC|2940|
|TTTGGTGTCT|ATTTTCTCTT|CCATAAAAAA|AGCCTGACTC|CACTTCCCGC|GTTACTGAT|3000|
|TACTAGCGAA|GCTGCGGGTG|CATTTTTCA|AGATAAGGC|ATCCCGATT|ATATTCTATA|3060|
|CCGATGTGGA|TTGCGCATAC|TTTGTAACA|GAAAGTGATA|GCGTTGATGA|TTCTTCATTG|3120|
|GTCAGAAAAT|TATGAACGGT|TTCTTCTATT|TTGTCTCTAT|ATACTACGTA|TAGGAAATGT|3180|
|TTACATTTTC|GTATTGTTTT|CGATTCACTC|TATGAATAGT|TCTTACTACA|ATTTTTTTGT|3240|
|CTAAAGAGTA|ATACTAGAGA|TAAACATAAA|AAATGTAGAG|GTCGAGTTTA|GATGCAAGTT|3300|
|CAAGGAGCGA|AAGGTGGATG|GGTAGGTTAT|ATAGGGATAT|AGCACAGAGA|TATATAGCAA|3360|
|AGAGATACTT|TTGAGCAATG|TTTGTGGAAG|CGGTATTCGC| | |3400|

( 2 ) INFORMATION FOR SEQ ID NO: 4:

( i ) SEQUENCE CHARACTERISTICS:
        ( A ) LENGTH: 3249 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Saccharomyces cerevisiae ( i x ) FEATURE:
        ( A ) NAME/KEY: misc_recomb
        ( B ) LOCATION: 290..291

( i x ) FEATURE:
        ( A ) NAME/KEY: misc_recomb
        ( B ) LOCATION: 426..427

( i x ) FEATURE:
        ( A ) NAME/KEY: misc_recomb
        ( B ) LOCATION: 1213..1214

( i x ) FEATURE:
        ( A ) NAME/KEY: misc_recomb
        ( B ) LOCATION: 2143..2144

( x i ) SEQUENCE DESCRIPTION: SEQ ID NO: 4:

| | | | | | | |
|---|---|---|---|---|---|---|
| AATATTTTAG | TAGCTCGTTA | CAGTCCGGTG | CGTTTTTGGT | TTTTTGAAAG | TGCGTCTTCA | 60 |
| GAGCGCTTTT | GGTTTTCAAA | AGCGCTCTGA | AGTTCCTATA | CTTTCTAGCT | AGAGAATAGG | 120 |
| AACTTCGGAA | TAGGAACTTC | AAAGCGTTTC | CGAAAACGAG | CGCTTCCGAA | AATGCAACGC | 180 |
| GAGCTGCGCA | CATACAGCTC | ACTGTTCACG | TCGCACCTAT | ATCTGCGTGT | TGCCTGTATA | 240 |
| TATATATACA | TGAGAAGAAC | GGCATAGTGC | GTGTTTATGC | TTAAATGCGT | ATCCCGCAAG | 300 |
| AGGCCCGGCA | GTCAGGTGGC | ACTTTCGGG | GAAATGTGCG | CGGAACCCCT | ATTTGTTTAT | 360 |
| TTTTCTAAAT | ACATTCAAAT | ATGTATCCGC | TCATGAGACA | ATAACCCTGA | TAAATGCTTC | 420 |
| AATAATGATC | CACGAGATTT | CAGGAGCTAA | GGAAGCTAAA | ATGGAGAAAA | AAATCACTGG | 480 |
| ATATACCACC | GTTGATATAT | CCCAATGGCA | TCGTAAAGAA | CATTTGAGG | CATTTCAGTC | 540 |
| AGTTGCTCAA | TGTACCTATA | ACCAGACCGT | TCAGCTGGAT | ATTACGGCCT | TTTTAAAGAC | 600 |
| CGTAAAGAAA | AATAAGCACA | AGTTTTATCC | GGCCTTTATT | CACATTCTTG | CCCGCCTGAT | 660 |
| GAATGCTCAT | CCGGAGTTCC | GTATGGCAAT | GAAAGACGGT | GAGCTGGTGA | TATGGGATAG | 720 |
| TGTTCACCCT | TGTTACACCG | TTTTCCATGA | GCAAACTGAA | ACGTTTTCAT | CGCTCTGGAG | 780 |
| TGAATACCAC | GACGATTTCC | GGCAGTTTCT | ACACATATAT | TCGCAAGATG | TGGCGTGTTA | 840 |
| CGGTGAAAAC | CTGGCCTATT | TCCCTAAAGG | GTTTATTGAG | AATATGTTTT | TCGTCTCAGC | 900 |
| CAATCCCTGG | GTGAGTTTCA | CCAGTTTTGA | TTTAAACGTG | GCCAATATGG | ACAACTTCTT | 960 |
| CGCCCCCGTT | TTCACAATGG | GCAAGTATTA | TACGCAAGGC | GACAAGGTGC | TGATGCCGCT | 1020 |
| GGCGATTCAG | GTTCATCATG | CCGTTTGTGA | TGGCTTCCAT | GTCGGCAGAA | TGCTTAATGA | 1080 |
| ATTACAACAG | TACTGCGATG | AGTGGCAGGG | CGGGGCGTAA | TTTTTTTAAG | GCAGTTATTG | 1140 |
| GTGCCCTTAA | ACGCCTGGTG | CTACGCCTGA | ATAAGTGATA | ATAAGCGGAT | GAATGGCAGA | 1200 |
| AATTCGTCGG | ATCAAAGGA | TCTAGGTGAA | GATCCTTTTT | GATAATCTCA | TGACCAAAAT | 1260 |
| CCCTTAACGT | GAGTTTTCGT | TCCACTGAGC | GTCAGACCCC | GTAGAAAAGA | TCAAAGGATC | 1320 |
| TTCTTGAGAT | CCTTTTTTTC | TGCGCGTAAT | CTGCTGCTTG | CAAACAAAAA | AACCACCGCT | 1380 |
| ACCAGCGGTG | GTTTGTTTGC | CGGATCAAGA | GCTACCAACT | CTTTTTCCGA | AGGTAACTGG | 1440 |
| CTTCAGCAGA | GCGCAGATAC | CAAATACTGT | TCTTCTAGTG | TAGCCGTAGT | TAGGCCACCA | 1500 |
| CTTCAAGAAC | TCTGTAGCAC | CGCCTACATA | CCTCGCTCTG | CTAATCCTGT | TACCAGTGGC | 1560 |
| TGCTGCCAGT | GGCGATAAGT | CGTGTCTTAC | CGGGTTGGAC | TCAAGACGAT | AGTTACCGGA | 1620 |
| TAAGGCGCAG | CGGTCGGGCT | GAACGGGGGG | TTCGTGCACA | CAGCCCAGCT | TGGAGCGAAC | 1680 |
| GACCTACACC | GAACTGAGAT | ACCTACAGCG | TGAGCATTGA | GAAAGCGCCA | CGCTTCCCGA | 1740 |
| AGGGAGAAAG | GCGGACAGGT | ATCCGGTAAG | CGGCAGGGTC | GGAACAGGAG | AGCGCACGAG | 1800 |
| GGAGCTTCCA | GGGGGAAACG | CCTGGTATCT | TTATAGTCCT | GTCGGGTTTC | GCCACCTCTG | 1860 |
| ACTTGAGCGT | CGATTTTTGT | GATGCTCGTC | AGGGGGGCGG | AGCCTATGGA | AAAACGCCAG | 1920 |
| CAACGCGGCC | TTTTTACGGT | TCCTGGCCTT | TTGCTGGCCT | TTTGCTCACA | TGTTCTTTCC | 1980 |
| TGCGTTATCC | CCTGATTCTG | TGGATAACCG | TATTACCGCC | TTTGAGTGAG | CTGATACCGC | 2040 |
| TCGCCGCAGC | CGAACGACCG | AGCGCAGCGA | GTCAGTGAGC | GAGGAAGCGG | AAGAGCGCTA | 2100 |
| GCAGCACGCC | ATAGTGACTG | GCGATGCTGT | CGGAATGGAC | GATACTTGTT | ACCCATCATT | 2160 |
| GAATTTTGAA | CATCCGAACC | TGGGAGTTTT | CCCTGAAACA | GATAGTATAT | TTGAACCTGT | 2220 |
| ATAATAATAT | ATAGTCTAGC | GCTTTACGGA | AGACAATGTA | TGTATTTCGG | TTCCTGGAGA | 2280 |
| AACTATTGCA | TCTATTGCAT | AGGTAATCTT | GCACGTCGCA | TCCCCGGTTC | ATTTTCTGCG | 2340 |

-continued

| | | | | | | |
|---|---|---|---|---|---|---|
|TTTCCATCTT|GCACTTCAAT|AGCATATCTT|TGTTAACGAA|GCATCTGTGC|TTCATTTTGT|2400|
|AGAACAAAAA|TGCAACGCGA|GAGCGCTAAT|TTTTCAAACA|AAGAATCTGA|GCTGCATTTT|2460|
|TACAGAACAG|AAATGCAACG|CGAAAGCGCT|ATTTTACCAA|CGAAGAATCT|GTGCTTCATT|2520|
|TTTGTAAAAC|AAAATGCAA|CGCGAGAGCG|CTAATTTTTC|AAACAAGAA|TCTGAGCTGC|2580|
|ATTTTTACAG|AACAGAAATG|CAACGCGAGA|GCGCTATTTT|ACCAACAAAG|AATCTATACT|2640|
|TCTTTTTTGT|TCTACAAAAA|TGCATCCCGA|GAGCGCTATT|TTCTAACAA|AGCATCTTAG|2700|
|ATTACTTTTT|TTCTCCTTTG|TGCGCTCTAT|AATGCAGTCT|CTTGATAACT|TTTTGCACTG|2760|
|TAGGTCCGTT|AAGGTTAGAA|GAAGGCTACT|TTGGTGTCTA|TTTTCTCTTC|CATAAAAAAA|2820|
|GCCTGACTCC|ACTTCCCGCG|TTTACTGATT|ACTAGCGAAG|CTGCGGGTGC|ATTTTTTCAA|2880|
|GATAAAGGCA|TCCCCGATTA|TATTCTATAC|CGATGTGGAT|TGCGCATACT|TTGTAACAG|2940|
|AAAGTGATAG|CGTTGATGAT|TCTTCATTGG|TCAGAAAATT|ATGAACGGTT|TCTTCTATTT|3000|
|TGTCTCTATA|TACTACGTAT|AGGAAATGTT|TACATTTTCG|TATTGTTTTC|GATTCACTCT|3060|
|ATGAATAGTT|CTTACTACAA|TTTTTTTGTC|TAAAGAGTAA|TACTAGAGAT|AAACATAAAA|3120|
|AATGTAGAGG|TCGAGTTTAG|ATGCAAGTTC|AAGGAGCGAA|AGGTGGATGG|GTAGGTTATA|3180|
|TAGGGATATA|GCACAGAGAT|ATATAGCAAA|GAGATACTTT|TGAGCAATGT|TTGTGGAAGC|3240|
|GGTATTCGC| | | | | |3249|

( 2 ) INFORMATION FOR SEQ ID NO: 5:

( i ) SEQUENCE CHARACTERISTICS:
        ( A ) LENGTH: 1115 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Saccharomyces cerevisiae ( x i ) SEQUENCE DESCRIPTION: SEQ ID NO: 5:

| | | | | | | |
|---|---|---|---|---|---|---|
|TCGACGGATC|TGGCTTTTCA|ATTCAATTCA|TCATTTTTTT|TTTATTCTTT|TTTTGATTT|60|
|CGGTTTCCTT|GAAATTTTTT|TGATTCGGTA|ATCTCCGAAC|AGAAGGAAGA|ACGAAGGAAG|120|
|GAGCACGATT|TTTGCATGGT|ATATATACGG|ATATGTAGTG|TTGAAGAAAC|ATGAAATTGC|180|
|CCAGTATTCT|TAACCCAACT|GCACAGAACA|AAAACCGGAA|ACGAAGATAA|ATCATGTCGA|240|
|AAGCTACATA|TAAGGAACGT|GCTGCTACTC|ATCCTAGTCC|TGTTGCTGCC|AAGCTATTTA|300|
|ATATCATGCA|CGAAAAGCAA|ACAAACTTGT|GTGCTTCATT|GGATGTTCGT|ACCACCAAGG|360|
|AATTACTGGA|GTTAGTTGAA|GCATTAGGTC|CCAAAATTTG|TTTACTAAAA|ACACATGTGG|420|
|ATATCTTGAC|TGATTTTTCG|ATGGAGGGCA|CAGTTAAGCC|GCTAAAGGCA|TTATCCGCCA|480|
|AGTACAATTT|TTACTCTTC|GAAGACAGAA|AATTTGCTGA|CATTGGTAAT|ACAGTCAAAT|540|
|TGCAGTACTC|TGCGGGTGTC|TATAGAATAG|CAGAATGGGC|AGACATTACG|AATGCACACG|600|
|GTGTGGTGGG|CCCAGGTATT|GTTAGCGGTT|TGAAGCAGGC|GGCAGAAGAA|GTAACAAAGG|660|
|AACCTAGAGG|ACTTTTGATG|TTAGCAGAAT|TGTCATGCAA|GGGCTCCCTA|TCTACTGGAG|720|
|AATATACTAA|GGGTACTGTT|GACATTGCGA|AGAGCGACAA|AGATTTGTT|ATCGGCTTTA|780|
|TTGCTCAAAG|AGACATGGGT|GGAAGAGATG|AAGGTTACGA|TTGGTTGATT|ATGACACCCG|840|

| | | | | | |
|---|---|---|---|---|---|
| GTGTGGGTTT | AGATGACAAG | GGAGACGCAT | TGGGTCAACA | GTATAGAACC | GTGGATGATG | 900 |
| TGGTCTCTAC | AGGATCTGAC | ATTATTATTG | TTGGAAGAGG | ACTATTTGCA | AAGGGAAGGG | 960 |
| ATGCTAAGGT | AGAGGGTGAA | CGTTACAGAA | AAGCAGGCTG | GGAAGCATAT | TTGAGAAGAT | 1020 |
| GCGGCCAGCA | AAACTAAAAA | ACTGTATTAT | AAGTAAATGC | ATCTATACTA | AACTCACAAA | 1080 |
| TTAGAGCTTC | AATTTAATTA | TATCAGTTAT | TACCC | | | 1115 |

( 2 ) INFORMATION FOR SEQ ID NO: 6:

( i ) SEQUENCE CHARACTERISTICS:
( A ) LENGTH: 1334 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
( A ) ORGANISM: Saccharomyces cerevisiae ( x i ) SEQUENCE DESCRIPTION: SEQ ID NO: 6:

| | | | | | |
|---|---|---|---|---|---|
| AATTCCCATT | ATTTAAGGAC | CTATTGTTTT | TTCCAATAGG | TGGTTAGCAA | TCGTCTTACT | 60 |
| TTCTAACTTT | TCTTACCTTT | TACATTTCAG | CAATATATAT | ATATATTTCA | AGGATATACC | 120 |
| ATTCTAATGT | CTGCCCCTAT | GTCTGCCCCT | AAGAAGATCG | TCGTTTTGCC | AGGTGACCAC | 180 |
| GTTGGTCAAG | AAATCACAGC | CGAAGCCATT | AAGGTTCTTA | AAGCTATTTC | TGATGTTCGT | 240 |
| TCCAATGTCA | AGTTCGATTT | CGAAAATCAT | TTAATTGGTG | GTGCTGCTAT | CGACGCTACA | 300 |
| GGTGTCCCAC | TTCCAGATGA | GGCGCTGGAA | GCCTCCAAGA | AGGTTGATGC | CGTTTTGTTA | 360 |
| GGTGCTGTGG | GTGGTCCTAA | ATGGGGTACC | GGTAGTGTTA | GACCTGAACA | AGGTTTACTA | 420 |
| AAAATCCGTA | AAGAACTTCA | ATTGTACGCC | AACTTAAGAC | CATGTAACTT | TGCATCCGAC | 480 |
| TCTCTTTTAG | ACTTATCTCC | AATCAAGCCA | CAATTTGCTA | AAGGTACTGA | CTTCGTTGTT | 540 |
| GTCAGAGAAT | TAGTGGGAGG | TATTTACTTT | GGTAAGAGAA | AGGAAGACGA | TGGTGATGGT | 600 |
| GTCGCTTGGG | ATAGTGAACA | ATACACCGTT | CCAGAAGTGC | AAAGAATCAC | AAGAATGGCC | 660 |
| GCTTTCATGG | CCCTACAACA | TGAGCCACCA | TTGCCTATTT | GGTCCTTGGA | TAAAGCTAAT | 720 |
| GTTTTGGCCT | CTTCAAGATT | ATGGAGAAAA | ACTGTGGAGG | AAACCATCAA | GAACGAATTT | 780 |
| CCTACATTGA | AGGTTCAACA | TCAATTGATT | GATTCTGCCG | CCATGATCCT | AGTTAAGAAC | 840 |
| CCAACCCACC | TAAATGGTAT | TATAATCACC | AGCAACATGT | TTGGTGATAT | CATCTCCGAT | 900 |
| GAAGCCTCCG | TTATCCCAGG | TTCCTTGGGT | TTGTTGCCAT | CTGCGTCCTT | GGCCTCTTTG | 960 |
| CCAGACAAGA | ACACCGCATT | TGGTTTGTAC | GAACCATGCC | ACGGTTCTGC | TCCAGATTTG | 1020 |
| CCAAAGAATA | AGGTTGACCC | TATCGCCACT | ATCTTGTCTG | CTGCAATGAT | GTTGAAATTG | 1080 |
| TCATTGAACT | TGCCTGAAGA | AGGTAAGGCC | ATTGAAGATG | CAGTTAAAAA | GGTTTTGGAT | 1140 |
| GCAGGTATCA | GAACTGGTGA | TTTAGGTGGT | TCCAACAGTA | CCACCGAAGT | CGGTGATGCT | 1200 |
| GTCGCCGAAG | AAGTTAAGAA | AATCCTTGCT | TAAAAAGATT | CTCTTTTTTT | ATGATATTTG | 1260 |
| TACATAAACT | TTATAAATGA | AATTCATAAT | AGAAACGACA | CGAAATTACA | AAATGGAATA | 1320 |
| TGTTCATAGG | GTAG | | | | | 1334 |